United States Patent
Choo et al.

(10) Patent No.: US 6,912,438 B2
(45) Date of Patent: Jun. 28, 2005

(54) USING SCATTEROMETRY TO OBTAIN MEASUREMENTS OF IN CIRCUIT STRUCTURES

(75) Inventors: Bryan K. Choo, Mountain View, CA (US); Bhanwar Singh, Morgan Hill, CA (US); Ramkumar Subramanian, Sunnyvale, CA (US); Bharath Rangarajan, Santa Clara, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/277,016

(22) Filed: Oct. 21, 2002

(65) Prior Publication Data

US 2004/0078108 A1 Apr. 22, 2004

(51) Int. Cl.⁷ ............................................... G06F 19/00
(52) U.S. Cl. ...................................... 700/121; 430/296
(58) Field of Search .............................. 700/121, 117; 356/601, 124; 250/237; 430/22, 296, 942, 966

(56) References Cited

U.S. PATENT DOCUMENTS

| | | | |
|---|---|---|---|
| 6,429,930 B1 * | 8/2002 | Littau et al. ............... | 356/124 |
| 6,455,212 B1 * | 9/2002 | Honeycutt et al. ............ | 430/22 |
| 2002/0018217 A1 * | 2/2002 | Weber-Grabau et al. .... | 356/601 |
| 2002/0158193 A1 * | 10/2002 | Sezginer et al. ........ | 250/237 G |

FOREIGN PATENT DOCUMENTS

WO    WO 01/97279 A2    12/2001

OTHER PUBLICATIONS

International Search Report, PCT/US 03/32656, mailed May 19, 2004.
J.R. McNeil, "Scatterometry Applied to Microelectronics Processing—Part 1", Solid State Technology, Mar. 1, 1993, pp 29–30 and 32, vol. 36, No. 3, Cowan Publishing Corporation, Washington, United States.

* cited by examiner

Primary Examiner—Leo Picard
Assistant Examiner—Charles Kasenge
(74) Attorney, Agent, or Firm—Amin & Turocy, LLP

(57) ABSTRACT

A system and methodology are disclosed for monitoring and controlling a semiconductor fabrication process. Measurements are taken in accordance with scatterometry based techniques of repeating in circuit structures that evolve on a wafer as the wafer undergoes the fabrication process. The measurements can be employed to generate feed forward and/or feedback control data that can utilized to selectively adjust one or more fabrication components and/or operating parameters associated therewith to adapt the fabrication process. Additionally, the measurements can be employed in determining whether to discard the wafer or portions thereof based on a cost benefit analysis, for example. Directly measuring in circuit structures mitigates sacrificing valuable chip real estate as test grating structures may not need to be formed within the wafer, and also facilitates control over the elements that actually affect resulting chip performance.

25 Claims, 15 Drawing Sheets

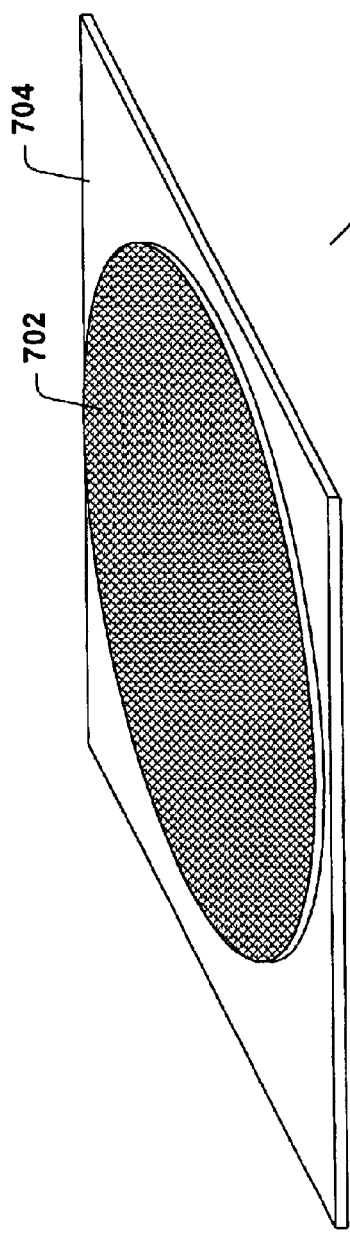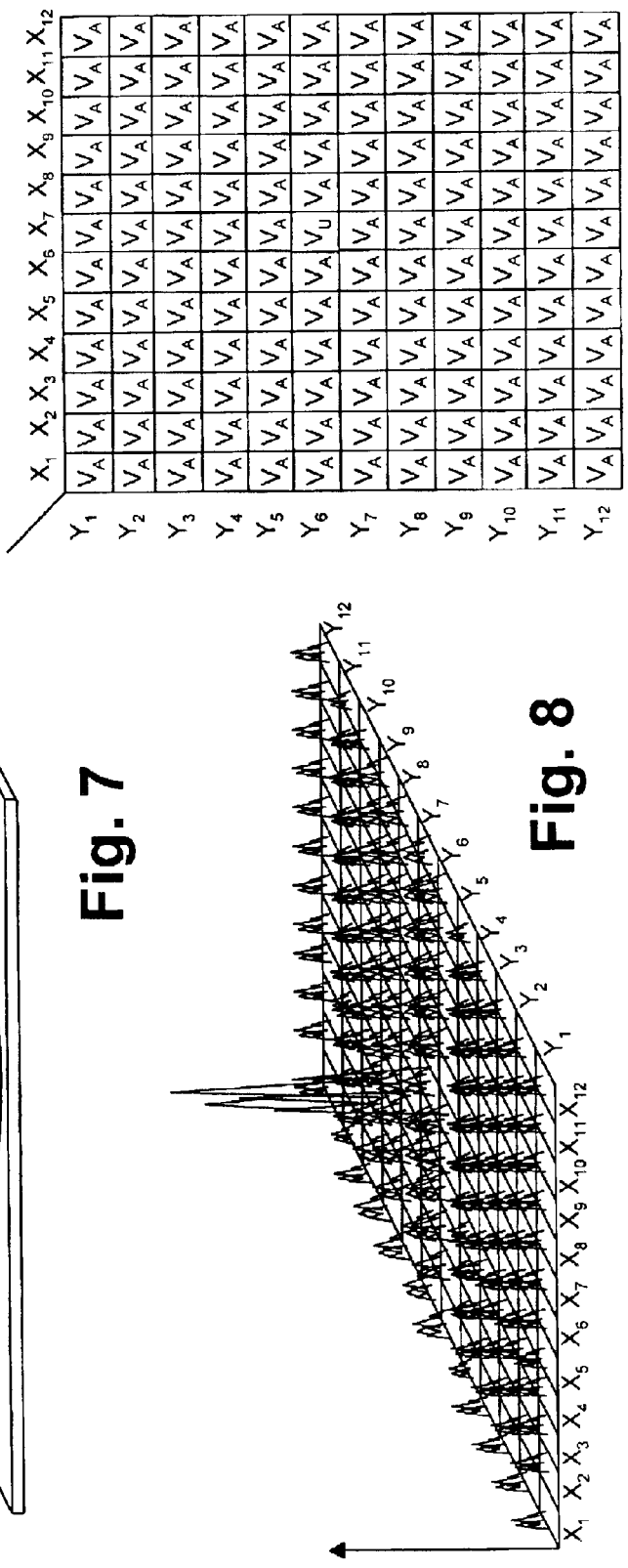
Fig. 7
Fig. 8
Fig. 9

USING SCATTEROMETRY TO OBTAIN MEASUREMENTS OF IN CIRCUIT STRUCTURES

TECHNICAL FIELD

The present invention generally relates to monitoring and/or controlling a semiconductor fabrication process, and in particular to a system and methodology for obtaining measurements of in circuit structures forming during the fabrication process and controlling the fabrication process in response to the measurements.

BACKGROUND

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature and structure sizes are required in integrated circuits (ICs) fabricated on small rectangular portions of the wafer, commonly known as dies. This may include the width and spacing of interconnecting lines, spacing and diameter of contact holes, the surface geometry such as corners and edges of various structures as well as the surface geometry of other features. To scale down device dimensions, more precise control of fabrication processes are required. The dimensions of and between circuit structures can be referred to as critical dimensions (CDs). Reducing CDs, and reproducing more accurate CDs facilitates achieving higher device densities through scaled down circuit structures and increased packing densities.

The process of manufacturing semiconductors or ICs typically includes more than a hundred steps (e.g., exposing, baking, developing), during which hundreds of copies of an integrated circuit may be formed on a single wafer, and more particularly on each die of a wafer. In many of these steps, material is overlayed or removed from existing layers at specific locations to form desired circuit structures or elements. Generally, the manufacturing process involves creating several patterned layers on and into a substrate that ultimately forms the complete integrated circuit. This layering process creates electrically active regions in and on the semiconductor wafer surface. The layer to layer alignment and isolation of such electrically active regions affects the precision with which structures can be formed on a wafer. If the layers are not aligned within acceptable tolerances, overlay errors can occur compromising the performance of the electrically active regions and adversely affecting chip reliability.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its purpose is merely to present some concepts of the invention in a simplified form as a prelude to the more detailed description that is presented later.

According to one or more aspects of the present invention, measurements of repeating in circuit structures formed on a wafer during a semiconductor fabrication process are taken by a system employing scatterometry based techniques. The measurements can be utilized to generate feed forward and/or feedback control data that can utilized to selectively adjust one or more fabrication components and/or operating parameters associated therewith to achieve desired results (e.g., critical dimensions within acceptable tolerances and/or mitigation of overlay). Additionally, the measurements can be employed in determining whether to discard the wafer or portions thereof based on a cost benefit analysis, for example. Directly measuring in circuit structures mitigates sacrificing valuable chip real estate as test grating structures may not need to be formed within the wafer.

More particularly, in accordance with one aspect of the invention, advantage is taken of uniformity associated with repeating patterns in connection with a semiconductor manufacturing process. A priori knowledge that particular features in a fabrication process process provides for multi-level inspection and defect detection. Rather than performing a detailed device by device inspection, such aspect of the present invention provides for performing a high-level inspection to search for irregularities with respect to an expected repeating pattern. If an irregularity is detected, a closer level inspection can be performed at the point of irregularity. Accordingly, more rapid inspection can be performed with respect to such portions of a wafer.

To the accomplishment of the foregoing and related ends, certain illustrative aspects of the invention are described herein in connection with the following description and the annexed drawings. These aspects are indicative, however, of but a few of the various ways in which one or more of the principles of the invention may be employed and the present invention is intended to include all such aspects and their equivalents. Other advantages and novel features of the invention will become apparent from the following detailed description of the invention when considered in conjunction with the drawings.

BRIEF DESCRIPTION OF THE DRAWINGS

FIG. 7 illustrates a perspective view of a grid mapped wafer according to one or more aspects of the present invention.

FIG. 8 illustrates plots of measurements taken at grid mapped locations on a wafer in accordance with one or more aspects of the present invention.

FIG. 9 illustrates a table containing entries corresponding to measurements taken at respective at grid mapped locations on a wafer in accordance with one or more aspects of the present invention.

DETAILED DESCRIPTION OF THE INVENTION

Figure 1:
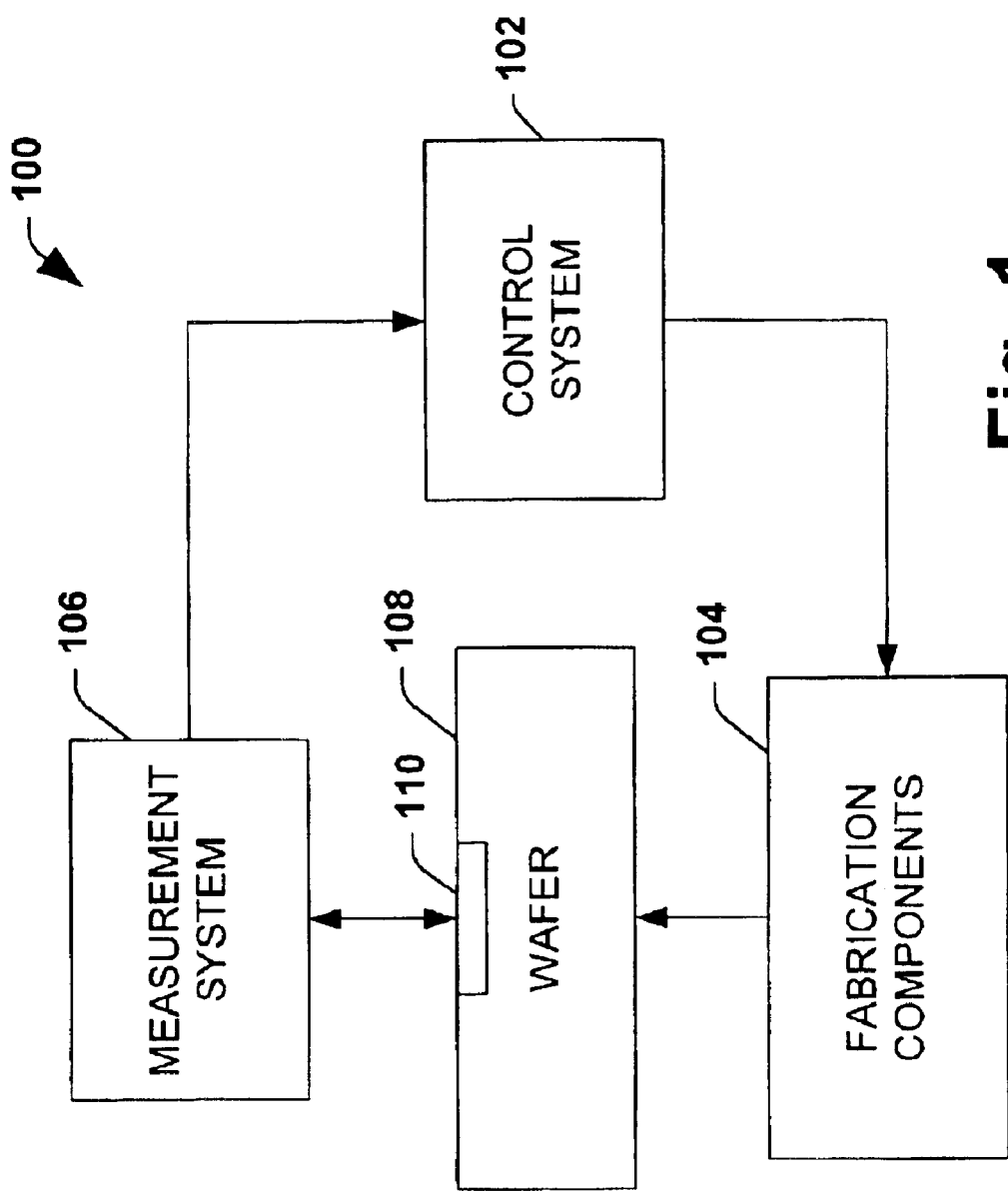
FIG. 1 is a block diagram schematically illustrating at a high level a system for monitoring and controlling a semiconductor fabrication process in accordance with one or more aspects of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that one or more aspects of the present invention may be practiced with a lesser degree of these specific details. In other instances, well-known structures and devices are shown in block diagram form in order to facilitate describing one or more aspects of the present invention.

The term "component" as used herein includes computer-related entities, either hardware, a combination of hardware and software, software, or software in execution. For example, a component may be a process running on a processor, a processor, an object, an executable, a thread of execution, a program and a computer. By way of illustration, both an application running on a server and the server can be components. By way of further illustration, both a stepper and a process controlling the stepper can be components.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed.

FIG. 1 illustrates a system 100 for monitoring and controlling an integrated circuit (IC) fabrication process according to one or more aspects of the present invention. The system 100 includes a control system 102, fabrication components 104 of the process, a measurement system 106 and a wafer 108 undergoing the fabrication process. As is typical with many semiconductor fabrication schemes, one or more repeating in circuit structures 10 are formed on the wafer 108 during the fabrication process. The control system 102 is operatively coupled to the measurement system 106 and the fabrication components 104 to regulate the fabrication process in response to readings taken by the measurement system. In particular, the control system 102 selectively controls one or more of the fabrication components 104 and/or one or more operating parameters associated therewith via feed forward and/or feedback control data generated from information obtained by the measurement system 106. The present invention can employ the repeating device structures in lieu of conventional grating structures in connection with particular quality assurance and monitoring methodologies.

The measurement system 106 can include for example a scatterometry system (not shown) for measuring one or more aspects (e.g., critical dimensions and/or overlay) of the repeating circuit structures forming within the wafer during the fabrication process. Since the circuit structures are themselves measured, sacrificial use of valuable chip real estate can be mitigated as the number of test gratings required can be reduced and in some cases eliminated from being formed within/on the wafer. The measurements yield information about the structures that actually affect device performance, whereas test gratings, in general, merely yield generalized information about the fabrication process. The lack of test gratings also mitigates time and equipment requirements associated with forming the test gratings in the wafer (e.g., usually within scribe lines within the wafer). The measurements can thus be utilized to monitor and control the fabrication process, while mitigating the amount of chip real estate, time and equipment required for the fabrication process.

It is to be appreciated that any of a variety of fabrication components and/or operating parameters associated therewith can be selectively adapted by the control system 102 based upon the readings taken by the measurement system 106. By way of example and not limitation, this can include, but is not limited to, temperatures associated with the process, pressures associated with the process, concentration of gases and chemicals within the process, composition of gases, chemicals and/or other ingredients within the process, flow rates of gases, chemicals and/or other ingredients within the process, timing parameters associated with the process and excitation voltages associated with the process. By way of further example, parameters associated with high-resolution photolithographic components utilized to develop integrated circuits (ICs) with small closely spaced apart features can be controlled to achieve desired results. In general, lithography refers to processes for pattern transfer between various media, and in semiconductor fabrication a silicon slice, the wafer, is coated uniformly with a radiation-sensitive film, the photoresist. The photoresist coated substrate is baked to evaporate any solvent in the photoresist composition and to fix the photoresist coating onto the substrate. An exposing source (such as light, x-rays, or an electron beam) illuminates selected areas of the surface of the film through an intervening master template for a particular pattern. The lithographic coating is generally a radiation-sensitized coating suitable for receiving a projected image of the subject pattern. Once the image from the intervening master template is projected onto the photoresist, it is indelibly formed therein.

Light projected onto the photoresist layer during photolithography changes properties (e.g., solubility) of the layer such that different portions thereof (e.g., the illuminated or un-illuminated portions, depending upon the photoresist type) can be manipulated in subsequent processing steps. For example, regions of a negative photoresist become insoluble when illuminated by an exposure source such that the application of a solvent to the photoresist during a subsequent development stage removes only non-illuminated regions of the photoresist. The pattern formed in the negative photoresist layer is, thus, the negative of the pattern defined by opaque regions of the template. By contrast, in a positive photoresist, illuminated regions of the photoresist become soluble and are removed via application of a solvent during development. Thus, the pattern formed in the positive photoresist is a positive image of opaque regions on the template. Controlling the degree to which a photoresist is exposed to illumination (e.g., time, intensity) can thus affect the fidelity of pattern transfer and resulting circuit structures. For example, overexposure can create features that are deeper than desired, while underexposure can create features that are shallower than desired. The subject invention via monitoring in part formation of repeating structures can facilitate regulating various aspects of a seminconductor fabrication process to converge toward achieving a desired result.

The type of illumination utilized to transfer the image onto a wafer can also be controlled to affect critical dimensions and pattern transfer. For instance, as feature sizes are driven smaller and smaller, limits are approached due to the wavelengths of optical radiation utilized. As such, the type of radiation and thus the wavelengths of radiation can be regulated to control pattern transfer. For instance, radiation having more conducive wavelengths (e.g., extreme ultraviolet (EUV) and deep ultraviolet (DUV) radiation having wavelengths within the range of 5–200 nm) can be utilized for lithographic imaging in an effort to accurately achieve smaller feature sizes. However, such radiation can be highly absorbed by the photoresist material. Consequently, the penetration depth of the radiation into the photoresist can be limited. The limited penetration depth requires use of ultra-thin photoresists so that the radiation can penetrate the entire depth of the photoresist in order to effect patterning thereof. The performance of circuits formed through photolithographic processing is, thus, also affected by the thickness of photoresist layers. The thickness of photoresist layers can be reduced through chemical mechanical polishing (CMP). In general, CMP employs planarization techniques wherein a surface is processed by a polishing pad in the presence of an abrasive or non-abrasive liquid slurry. The slurry employed reacts with the photoresist at the surface/subsurface range. Preferably the degree of reaction is not great enough to cause rapid or measurable dissolution (e.g., chemical etching) of the photoresist, but merely sufficient to cause a minor modification of chemical bonding in the photoresist adequate to facilitate surface layer removal by applied mechanical stress (e.g., via use of a CMP polishing pad). Thus, the concentration, rate of flow and degree of abrasiveness of slurry applied during CMP as well as the amount of pressure applied between a polishing pad and wafer can be regulated to control semiconductor fabrication processing.

Depending upon the resist system utilized, post exposure baking may also be employed in semiconductor fabrication to affect image transfer by activating chemical reactions in the photoresist. The temperatures and/or times that portions of the wafer are exposed to particular temperatures can be controlled to regulate the uniformity of photoresist hardening (e.g., by reducing standing wave effects and/or to thermally catalyze chemical reactions that amplify the image). Higher temperatures can cause faster baking and faster hardening, while lower temperatures can cause slower baking and correspondingly slower hardening, which can affect structure uniformity by altering, for example, the consistency of a line width. Accordingly, time and temperature parameters can also be controlled during post exposure baking.

Operating parameters of an etching stage can similarly be controlled to achieve desired results. After illumination, the pattern image is transferred into the wafer from the photoresist coating in an etching stage wherein an etchant, as well as other ingredients, are applied to the surface of the wafer by an excitation voltage or otherwise. The etchant removes or etches away portions of the wafer exposing during the development process. Portions of the wafer under less soluble areas of the photoresist are protected from the etchants. The less soluable portions of the photoresist are those portions that are not affected by the developer during the development process and that are not affected by the etchant during the etching process. These insoluble portions of the photoresist are removed in subsequent processing stage(s) to completely reveal the wafer and the pattern(s) formed therein. The concentration of materials utilized in etching can thus be controlled to achieve desired results by affecting the accuracy with which selected portions of the wafer are etched away.

Parameters relating to the type of template utilized to transfer an image onto a wafer can also be controlled to affect critical dimensions, layer to layer alignment and overlay. Where the template is a reticle, for instance, the pattern is transferred to only one (or a few) die per exposure, as opposed to where the template is a mask and all (or most) die on the wafer are exposed at once. Multiple exposures through a reticle are often performed in a step and scan fashion, wherein after each exposure, a stage to which the wafer is mounted is moved or stepped to align the next die for exposure through the reticle. This process may need to be performed as many times as there are die in the wafer. Thus, stepper movement can be controlled to facilitate achieving desired results. The pattern formed within the reticle is often an enlargement of the pattern to be transferred onto the wafer. This allows more detailed features to be designed within the reticle. Energy from light passed through the reticle can, however, heat the reticle when the image is exposed onto the wafer. This can cause mechanical distortions in the reticle due to thermal expansion and/or contraction of the reticle. Such distortions may alter the geometry of intricate circuit structures (e.g., by narrowing a line) and/or interfere with layer to layer registration to such a degree that a resulting circuit does not operate as planned when the image is transferred onto the wafer. Moreover, since the pattern is usually an enlargement of the pattern to be transferred onto the wafer, it typically has to be reduced (e.g., via a de-magnifying lens system) during the lithographic process. Shrinking an already distorted feature (e.g., a narrowed line) can have a deleterious effect on repeating structures. Thus, while such a template may be effective to transfer more intricate pattern designs, it calls for highly accurate alignment and imaging. Temperature controls can thus be employed to mitigate thermally induced mechanical distortions that can adversely affect pattern transfers.

Additionally, parameters relating to film growth or deposition components (e.g., producing metals, oxides, nitrides, poly, oxynitrides or insulators) can be controlled to facilitate desired fabrication processing. Such films can be formed through thermal oxidation and nitridation of single crystal silicon and polysilicon, the formation of silicides by direct reaction of a deposited metal and the substrate, chemical vapor deposition (CVD), physical vapor deposition (PVD), low pressure CVD (LPCVD), plasma enhanced CVD (PECVD), rapid thermal CVD (RTCVD), metal organic chemical vapor deposition (MOCVD) and pulsed laser deposition (PLD). The rates of flow, temperature, pressures, concentrations and species of materials supplied during the semiconductor fabrication process can thus be regulated to govern film formation which bears on resulting in circuit structures.

Thus, as can be appreciated via the above, monitoring for repeating structures (e.g., formation thereof as well as resulting structures) in conection with feedback control and adapative regulating of various parameters relating to device fabrication can result in improving an overall semiconductor fabrication process.

Moreover, as noted above, inspection/monitoring in conection with the subject invention can facilitate efficient utilization of inspection equipment and processing time associated therewith. Rather than individually inspecting each independent device, the subject invention can facilitate mitigation of such convention highly granular inspection by allowing for high-pass inspection of certain areas of a wafer or device or represted circuit structures are expected. Such high-pass inspection can be performed to search for deviations from an expected repeating pattern as compared to deviations on a device bu device basis which can be time consuming as well as expensive from computational resource utilization perspective. Upon detecting a deviation from an expected repeating pattern, a more granular inspection cen be performed by the subject invention at the local of the point of irregularity.

Figure 2:
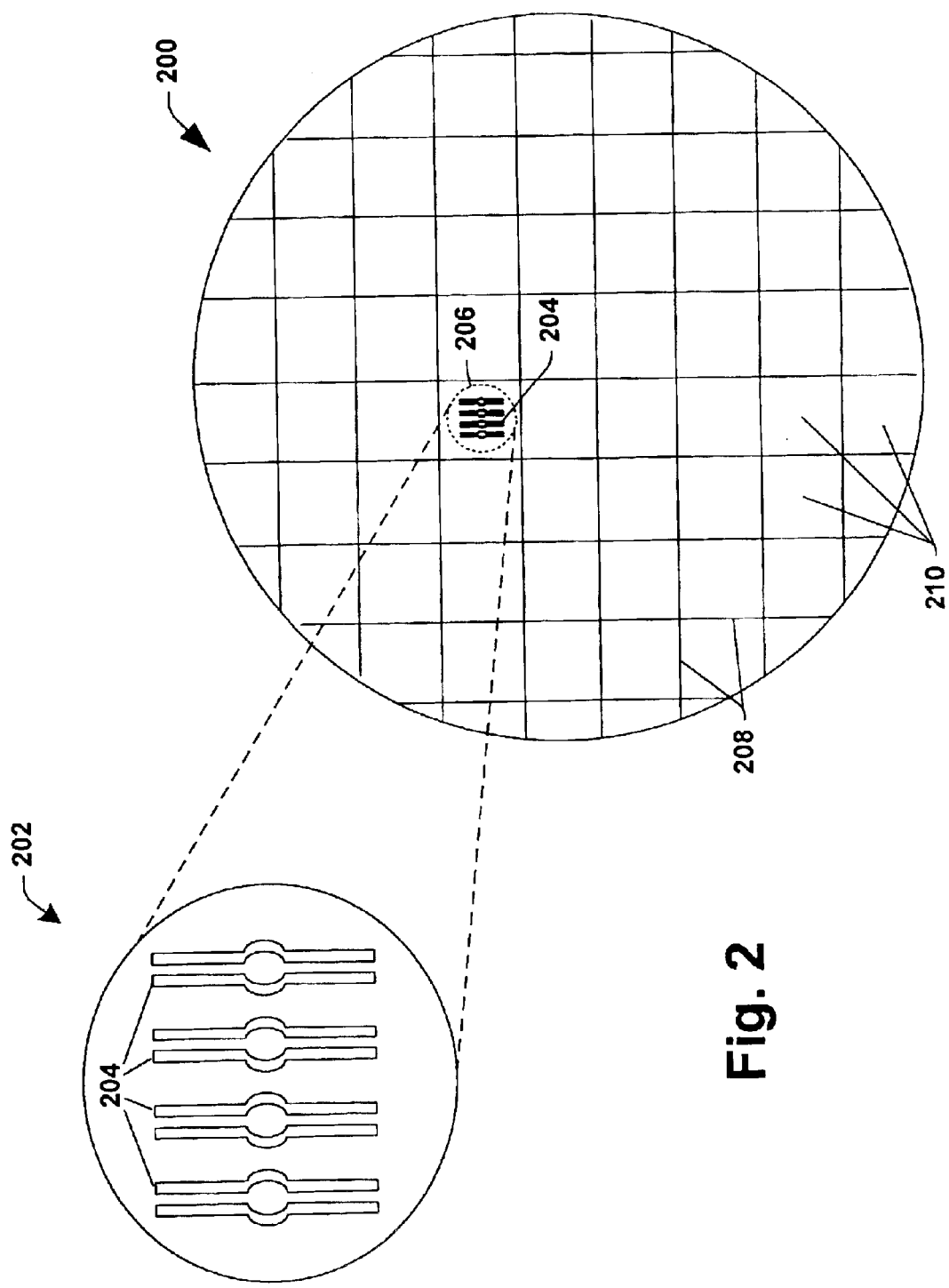
FIG. 2 illustrates a top view of a wafer and an enlargement of in circuit repeating structures formed on the wafer as the wafer undergoes a semiconductor fabrication process.

Turning to FIG. 2, a top view of a substrate 200 (e.g., a wafer) and an enlargement of in circuit repeating structures 202 that are formed on a portion 206 (e.g., a die) of the wafer 200 as the wafer undergoes a semiconductor fabrication process is illustrated. The repeating structures 204 can, for example, correspond to structures in a memory core area of an IC. The structures 204 comprise substantially elongated marks oriented substantially in parallel with one another and can be measured periodically throughout the fabrication process to determine if the process is proceeding as intended. By way of example, critical dimensions such as respective feature heights of each of the in circuit repeating structures can be measured to determine if the structures are being formed uniformly. The structures are similar to parallel fixed test grating structures that can be implemented as raised portions in the substrate or as troughs etched into the substrate, and which can be measured to obtain generalized information about the fabrication process. Forming test such grating structures near circuitry in the substrate, however, requires sacrificing areas of valuable chip real estate. As such, grating structures are often formed within scribe lines 208 in the wafer, which are unused areas of the wafer wherein no circuitry is formed, and which are located between individual chips allowing the chips 210 to be separated from the wafer after the fabrication process has been completed. Regardless of where the gratings are formed, however, since they are not part of the circuitry fabricated on the wafer, they do not reveal particular information about the elements that directly affect device performance. Directly measuring in circuit structures as with aspects of the present invention, on the other hand, yields highly relevant information about the elements that have a direct impact on resulting device performance. Accordingly, these measurements can be utilized to determine how to adjust the fabrication process to accurately and consistently produce devices having desired performance capabilities and reliability. It is to be appreciated that more complex (e.g., nonlinear) repeating in circuit structures could also be measured in accordance with one or more aspects of the present invention to monitor and control the fabrication process.

Figure 3:
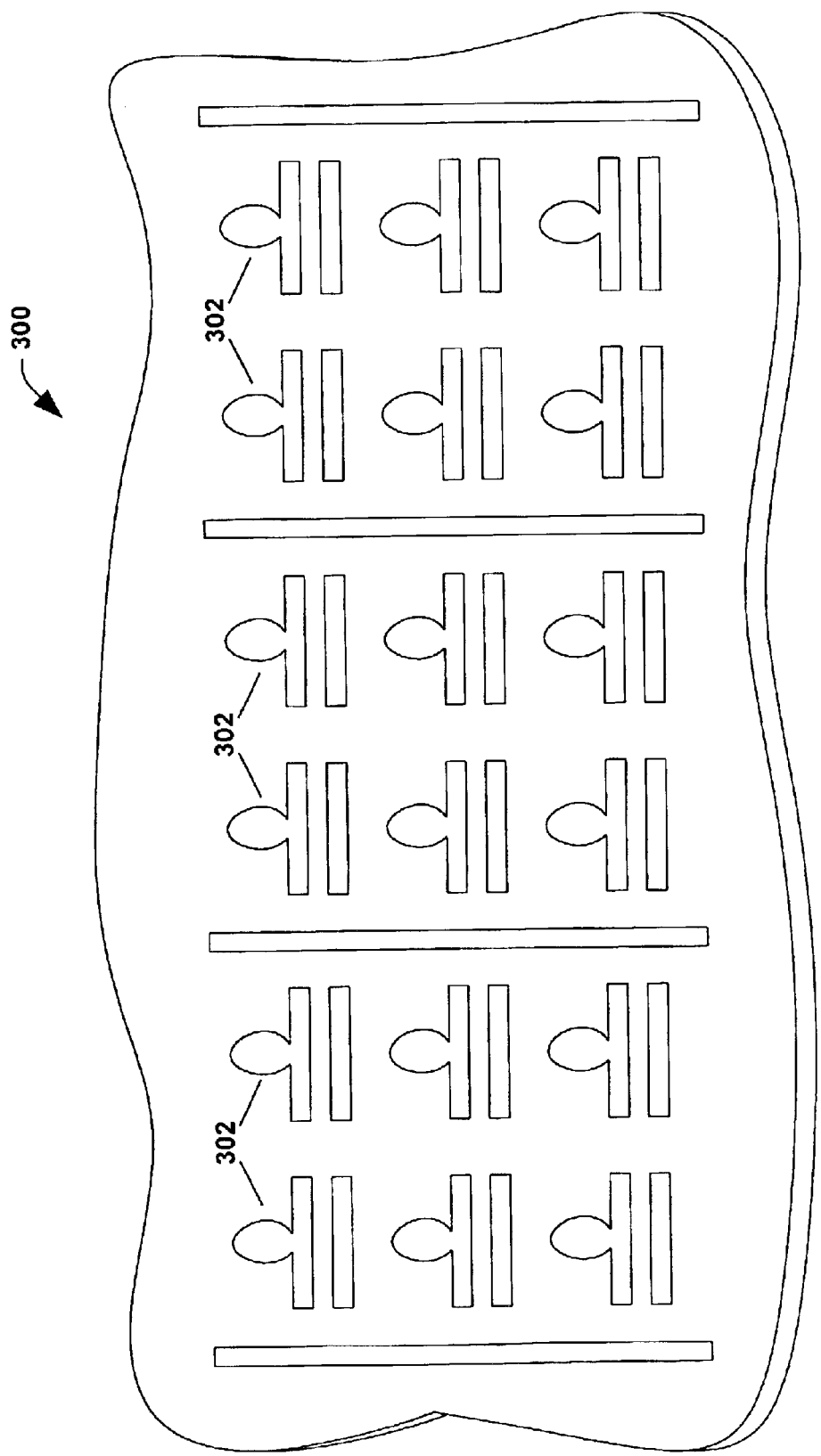
FIG. 3 is a perspective view of a portion of a wafer having formed thereon an example of other repeating in circuit structures that can be measured in monitoring and controlling a semiconductor fabrication process in accordance with one or more aspects of the present invention.

FIG. 3 illustrates a wafer 300 having formed thereon an example of other repeating in circuit structures 302 that can be measured in monitoring and controlling a semiconductor fabrication process in accordance with one or more aspects of the present invention. The structures 302 can, for example, comprise components of an SRAM memory cell formed on a wafer die as the wafer 300 matriculates through the fabrication process. The wafer 300 is depicted as broken away so as to present a greatly enlarged view of the structures 302. The area of the wafer 300 depicted can, for example, correspond to a portion of a die on the wafer wherein one or more SRAM memory cells can be formed. It will be appreciated that die on a wafer can include any number of integrated circuits (ICs) having one or more repeating circuit structures formed thereon as the fabrication process progresses. Aspects of these repeating structures (e.g., critical dimensions and/or overlay) can be measured periodically to determine if the fabrication process is proceeding as desired (e.g., whether the repeating structures are being produced uniformly). These measurements can be utilized to develop feed forward and/or feedback control data to adapt the fabrication process accordingly to mitigate undesired results.

Figure 4:
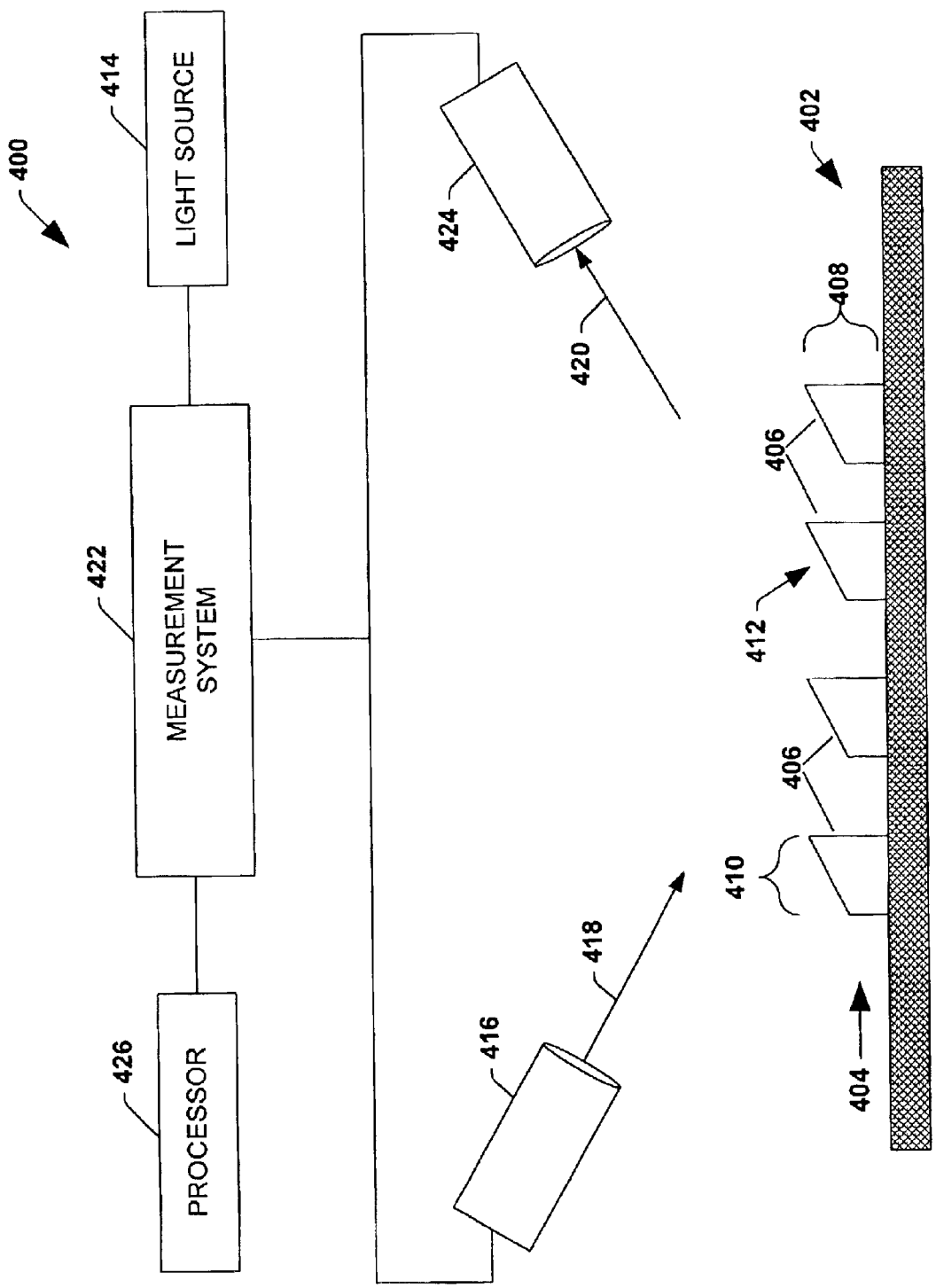
FIG. 4 illustrates a portion of a system effective to monitor the progress of a wafer matriculating through a semiconductor fabrication process in accordance with one or more aspects of the present invention.

FIG. 4 illustrates a portion of a system 400 being employed to monitor (e.g., via scatterometry) a wafer 402 matriculating through a semiconductor fabrication process in accordance with one or more aspects of the present invention. It will be appreciated that only a small portion (e.g., a single die) of the wafer 402 is depicted in FIG. 4 for purposes of simplicity. A cross sectional side view of the wafer 402 reveals a layer 404 on the wafer having in circuit repeating structures 406 formed therein. The repeating structures 406 are formed in the wafer 402 as the wafer progresses through the fabrication process to produce one or more integrated circuits (or portions thereof) on the wafer. The repeating structures 406 can, for example, make up portions of SRAM cells or memory core areas formed within portions (e.g., die) of the wafer.

In accordance with one or more aspects of the present invention, scatterometry based techniques can be employed to measure one or more dimensions of the structures 406 at various points in the IC fabrication process to determine what effect, if any, different components of the fabrication process have had or are having on respective structure dimensions. Different structure heights 408, widths 410 and/or slopes 412 can, for example, be measured to generate different signatures that may be indicative of the effect that one or more processing components that are operating within particular parameters are having on the fabrication process. The measurements/signatures can be analyzed to generate feedback/feed forward information that can be utilized to adjust operating parameters of processing components to which the same or other die are/will be subjected to mitigate undesired results. For example, respective structure heights can be measured periodically to determine if the structures are being formed uniformly. If not, one or more fabrication components and operating parameters associated therewith can be adapted accordingly based upon feedback/feed forward control data derived from the measurements. For instance, the volume, degree of abrasiveness and locations of slurry selectively distributed onto the wafer and/or the degree of pressure applied between a polishing pad and the wafer during a chemical mechanical polishing (CMP) process can be adjusted to mitigate non-uniformity of the structure heights.

In the system 400, a light source 414 provides light to one or more light emitters 416 that direct a light 418 incident to the repeating in circuit structures 406 formed on the wafer 402 as the fabrication process progresses. Preferably, the light source 414 is a frequency stabilized laser, however, it will be appreciated that any laser or other light source (e.g., laser diode or helium neon (HeNe) gas laser) suitable for carrying out the present invention may be employed. The light 418 is reflected from the structures 408 as reflected light 420. The incident light 418 may be referred to as the reference beam, and thus the phase, intensity and/or polarization of the reference beam 418 may be recorded in a measurement system 422 to facilitate later comparisons to the reflected beam 420 (e.g., via signature comparison). As the fabrication process progresses the angle of the reflected light 420 from the structures 406 will vary in accordance with the evolving dimensions of the structures 406. Similarly, the intensity, phase and polarization properties of the specularly reflected light 420 may vary in accordance with the evolving dimensions. One or more light detecting components 424 collects the reflected light 420 and transmits the collected light, and/or data associated with the collected light, to the measurement system 422. Any one or more light detecting components 424 suitable for carrying out aspects of the present invention may be employed (e.g., photo detector, photo diodes) for collecting reflected light 420. The measurement system 422 forwards information from the detecting components to a processor 426, which may or may not be integral with the measurement system 422. The processor, or central processing unit (CPU), is programmed to control and carry out the various functions described herein. The processor 426 can be any of a plurality of processors, and the manner in which the processor can be programmed to carry out the functions described herein will be readily apparent to those having ordinary skill in the art based on the description provided herein. The reflected light 420 can, for example, be analyzed to generate one or more signatures that can be compared to one or more stored signatures to determine whether, for example, desired critical dimensions are being achieved and/or whether the structures are being formed uniformly, and thus whether, for example, feed forward and/or backward information should be generated and applied to selectively control and adjust one or more operating parameters of one or more IC fabrication components (e.g., alignment, post exposure baking, development, photolithography, etching, polishing, deposition) to adapt the fabrication process to achieve a desired result. It will be appreciated that a multitude of structures can be formed on the wafer 402 and/or die in the wafer during the fabrication process to produce any number of circuits and/or circuitry components. Accordingly, the system 400 can be configured and operated (e.g., via the processor) to seek out and obtain measurements from repeating in circuit structures forming within the wafer (e.g., to facilitate determining uniformity and consistency of processing and structure formation).

Figure 5:
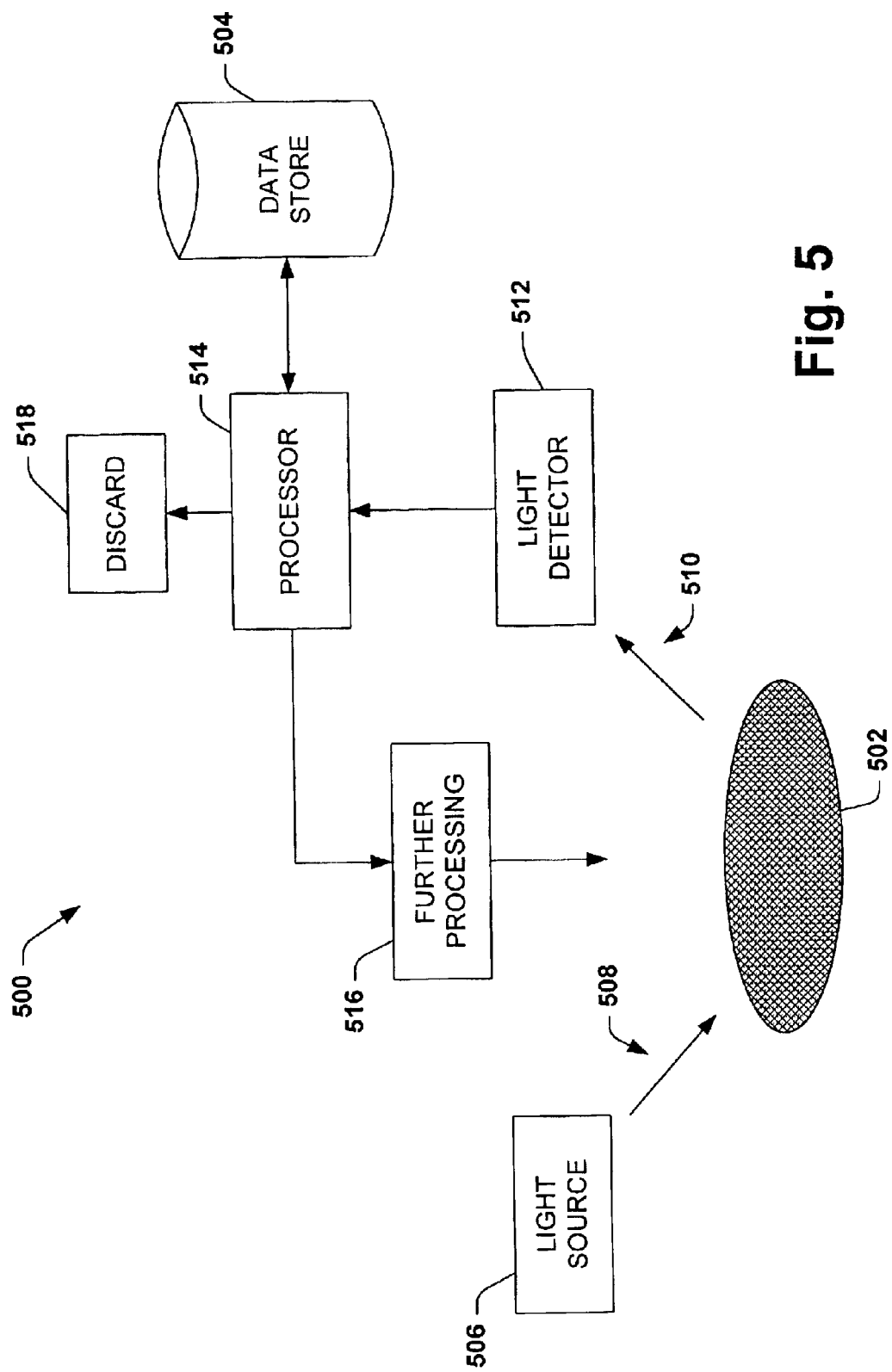
FIG. 5 illustrates a system for monitoring and controlling a semiconductor fabrication process according to one or more aspects of the present invention.

FIG. 5 illustrates a system 500 for monitoring and controlling a semiconductor fabrication process in accordance with one or more aspects of the present invention. The system 500 employs scatterometry based techniques to measure one or more repeating in circuit structures (not shown) forming within at least a portion (e.g., a die) on a wafer 502 during the fabrication process. The system can implement historical/test data, such as may be stored within a data store 504, to facilitate decision making and/or utilize current measurements to control the fabrication process in real time. It is to be appreciated that, to effectively adapt the fabrication process to achieve desired results, various aspects of the invention can employ technologies associated with facilitating unconstrained optimization and/or minimization of error costs, such as, for example, non-linear training systems/methodologies including, but not limited to back propagation, Bayesian, fuzzy sets, non-linear regression, or other neural networking paradigms including mixture of expert systems, cerebella model arithmetic computer (CMACS), radial basis functions, directed search networks and function link networks.

One or more light sources 506 direct light 508 incident to the wafer 502. It will be appreciated that a laser or any other suitable light source(s) can be employed in carrying out aspects of the present invention. For example, the light can originate from a frequency stabilized laser, a laser diode or a helium neon (HeNe) gas laser. It is to be appreciated that the light 508 can be directed at substantially all of the wafer simultaneously and/or at selected portions of the wafer throughout the fabrication process to spot check structures forming on the wafer, and to facilitate yielding determinations such as, for example, "defect present" or "defect free" at respective locations on the wafer 502.

The light 508 is reflected as reflected light 510 from the in circuit structures forming within the wafer 502 as the fabrication process progresses. The angle, phase, intensity and/or polarization of the reflected light 510 will vary in accordance with the evolving dimensions of the structures. The reflected light 510 is collected by one or more light detectors 512. The light detector(s) 512 comprise one or more light detecting devices and collect the light in accordance with scatterometry techniques.

Any of a number of light detectors can be utilized for carrying out aspects of the present invention. Some suitable detectors include, for example, photo diodes and photo detectors.

The reflected light 510 is communicated to a processor 514, which is operatively coupled to the light detector(s) 512. The processor 514 employs scatterometry based techniques to analyze, interpret and/or convert the reflected light 510 into data, such as, for example, signature data, numerical data and/or graphical data to facilitate further processing. Signatures can be generated, for example, by combining phase and/or intensity information associated with the reflected light 510.

It will be appreciated that the processor 514 can be any of a plurality of processors, and the manner in which the processor can be programmed to carry out the functions described herein will be readily apparent to those having ordinary skill in the art based on the description provided herein.

Depending upon the type of repeating in circuit structures analyzed by the system 500, library/database information can be implemented in adapting the fabrication process. By way of example, the structures illustrated in FIG. 3 may be more amenable to monitoring with database information since those structures comprise highly intricate patterns. The repeating in circuit structures illustrated in FIG. 2 on the other hand may be able to be monitored without stored data since they comprise substantially parallel linear markings. Differences between the linear structures depicted in FIG. 2 may be easily discerned, for example, whereas the more complex structures illustrated in FIG. 3 may need to be compared to stored data to reveal deviations from intended dimensions.

By way of example, the processor 514 can be programmed to compare (e.g., by pattern matching, interpolation or otherwise) one or more measured values to one or more stored values. The stored values can be maintained in the data store 504 and may include, for example, acceptable and unacceptable levels of non-uniformity, critical dimension tolerances, overlay tolerances, etc. By way of further example, the processor 514 can determine whether repeating in circuit structures have heights above a certain threshold level and/or whether the structures vary in height by more than a predetermined percentage, such that the structure dimensions are not coincident with that of optimal circuit layouts.

If a measured level of structural non-uniformity falls within a pre-defined acceptable range, then the processor 514 can, for example, direct the wafer 502 to additional/further processing 516. If, however, the level of non-uniformity, for example, exceeds a pre-defined range, then the processor 514 can direct the wafer 502 (or portions thereof) to be discarded 518 since the sheer amount of non-uniformity among repeating in circuit structures has rendered the wafer 502 or portions thereof unsalvageable. The determination to discard 518 the wafer may based upon, for example, a programmed cost-benefit analysis, Bayesian system neural network, rule based expert system, etc. For example, if the cost of repairing or reducing the non-uniformity outweighs the benefit received from such repair, then it could be determined that it would be more cost and time effective to simply discard the wafer 502, or portions thereof.

Additionally, or in the alternative, the processor 514 can selectively mark the wafer 502 or portions thereof for correction and determine what type of adjustments are to be made to particular fabrication components to effect the same. The processor 514 transmits these adjustments to the appropriate fabrication components (not shown) for the purpose of, for example, mitigating occurrences of non-uniform structure formation, or other undesirable processing, such as, critical dimensions falling outside of acceptable tolerances and/or the occurrence of overlay.

The processor 514 can, for example, be programmed to utilize non-linear training systems to determine the appropriate adjustments to make according to the information received from the detector(s) 512. This can be referred to as feedback/feed forward control data that facilitates achieving desired results. By way of example, if the structures are not uniform (e.g., have varying heights), the processor 514 may designate or mark certain portions of the wafer to undergo chemical mechanical polishing for particular durations in order to mitigate discarding the wafer. Furthermore, the processor 514 may produce control data that can be employed in regulating an etch process to etch back some structures. In the case of less than desired vertical thickness (e.g., height) of forming structures, the processor 514 may control a deposition process (e.g., by selectively adjusting the rate, concentration and/or mixture of gases distributed into a processing chamber) to cause more of the material forming the structure(s) to be deposited.

It will be appreciated that the processor 514 can also be programmed to cause the system to focus in on/take additional readings at portions of the wafer 502 where it is determined that repetition of in circuit structures is interrupted and/or where substantial changes in the structures are detected (e.g., in uniformity or otherwise) since abrupt changes in the repeating structures can affect resulting device performance and may be indicative of malfunctioning fabrication processes.

In addition, the system 500 can be employed in populating the data store 504 in a training stage, for example. In a training mode, the system 500 can generate substantially unique scatterometry signatures, which are stored in the data store 504. The data store 504 can be populated by presenting a series of wafers to the system, for instance. As such, the data store 504 can serve, for example, as a signal (signature) library that can be populated with an abundance of signatures against which one or more measurements can be compared. Alternatively, or in addition to manually observing values, simulation, modeling and/or artificial intelligence techniques can be employed to populate the data store with signatures against which measured values can be compared. It is to be appreciated that entries in the data store 504 can also, for example, be stored with/correlated with respective operating parameters under which they were obtained (e.g., illumination intensity, temperature, pressure, gas distribution volume/rate, timing parameters). As such, determinations made by comparing measurements to stored data can take into account the present value of one or more operating conditions such as temperature, pressure, etc. and the effects that these conditions are having on the fabrication process. It is to be further appreciated that the data store 504 can store data in data structures including, but not limited to one or more lists, arrays, tables, databases, stacks, heaps, linked lists and data cubes.

It will be appreciated that many of the components including the data store can, for example, reside in one physical or logical device (e.g., computer, process) and/or may be distributed between two or more physical or logical devices (e.g., disk drives, tape drives, memory units). The system 500 can thus be employed to provide in-situ measurements of production wafers and circuitry formed therein, thus providing advantages over conventional systems that facilitate only indirect measurements of the fabrication process via gratings formed in non-productive areas of the wafer, such as scribe lines, for example. The system 500 thus facilitates achieving higher quality semiconductors that exhibit greater consistency with respect to structure formation and performance.

Figure 6:
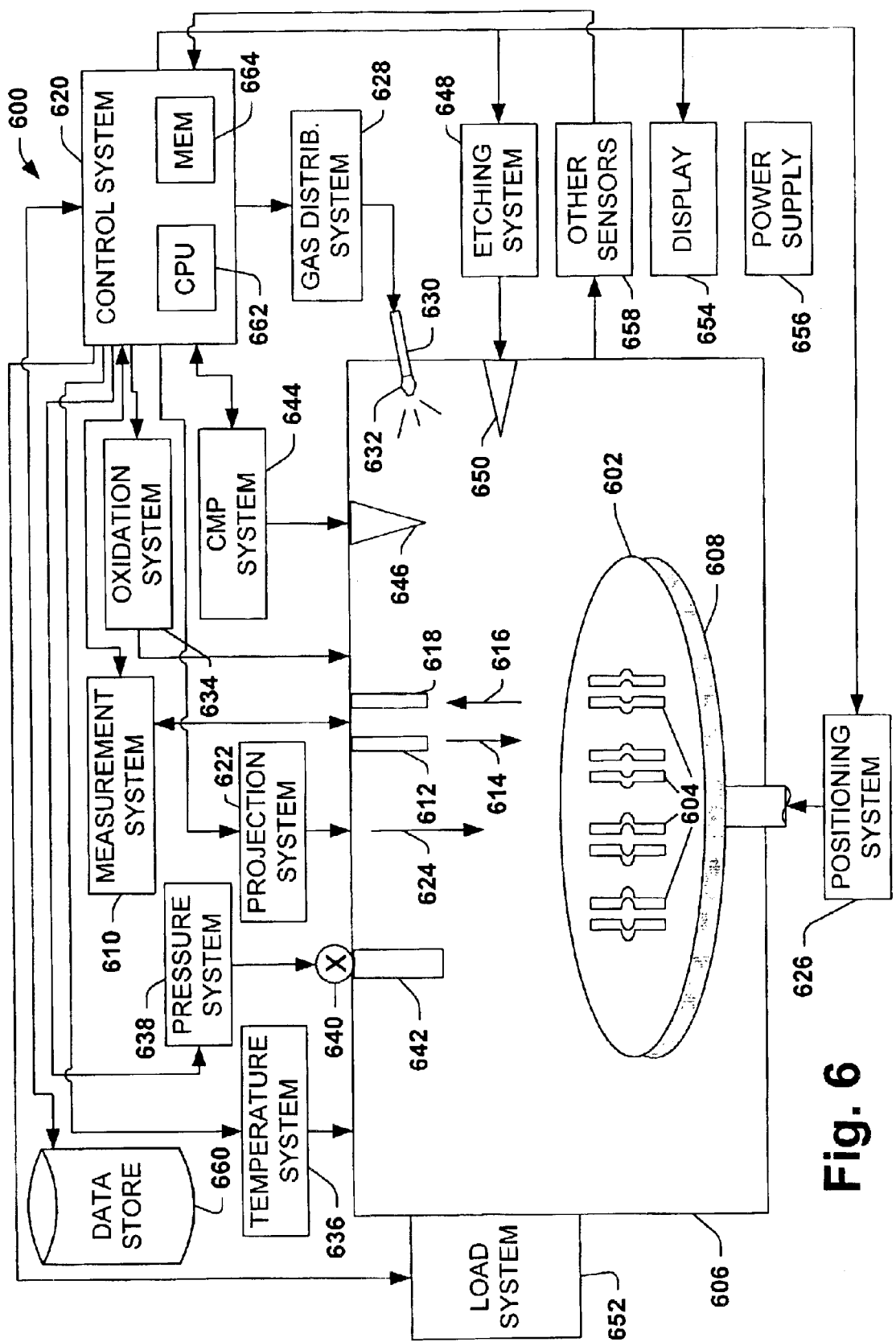
FIG. 6 illustrates another system for monitoring and controlling a semiconductor fabrication process in accordance with one or more aspects of the present invention.

FIG. 6 illustrates a system 600 for monitoring and controlling a semiconductor fabrication process according to one or more aspects of the present invention. A wafer 602, or a portion thereof (e.g., a die), is depicted as undergoing the fabrication process and has repeating in circuit structures 604 formed thereon. The structures are formed in the wafer as the wafer matriculates through the fabrication process and various components of the process act upon the wafer. The wafer is housed within a process chamber 606 and supported on a stage or chuck 608 (e.g., via vacuum).

The system 600 includes a measurement system 610 for monitoring the progress of the fabrication process according to scatterometry based techniques. The measurement system 610 has one or more light projecting sources 612 that project light 614 onto respective portions of the structures 604. It is to be appreciated that any suitable light source (e.g., frequency stabilized laser, laser diode or helium neon (HeNe) gas laser) can be employed for carrying out aspects of the present invention. Attributes (e.g., width, height, slope) of the structures cause the light to be reflected in different, quantifiable manners. Reflected light 616 is collected by one or more light detecting components 618. It will similarly be appreciated that any suitable light detecting components (e.g., photo detector, photo diodes) can be employed in carrying out aspects of the present invention. Readings taken by the measurement system can be employed in controlling the fabrication process. Information and data regarding the reflected light can, for example, be passed to a control system 620 and processed thereby to generate signatures, which can be utilized to facilitate feedback and/or feed-forward control signals for one or more fabrication components and/or operating parameters associated therewith as described herein to achieve desired results.

A projection system 622 is included such as to effect photolithographic processing by exposing the substrate to illumination 624 passed through a reticle (not shown). A positioning system 626 is also included and is operatively connected to the support 608 for selectively positioning the wafer 602 at desired position(s) within the chamber 606.

A gas distribution system 628 is operably coupled to the chamber 606 for selectively providing gaseous chemicals into the chamber at varying quantities to form film(s) on the substrate 602 based upon, among other things, the desired thickness/thinness of the films to be formed on the wafer, the size of the wafer and the volume of the chamber. By way of illustration, the gas distribution system 628 includes a source of a gaseous medium (a vapor) of one or more chemicals that are to be formed on the substrate. The gas is provided into the chamber through a conduit 630 that terminates in a nozzle 632. While, for purposes of brevity, a single nozzle 632 is shown in FIG. 6, it is to be appreciated that more than one nozzle or other gas delivery mechanisms may be utilized to provide gas into the chamber 606 at various mixtures and/or concentrations.

An oxidation system 634 also is provided for effecting oxidation within the processing chamber 606. For example, the oxidation system 634 can be a diffusion type system including a horizontal and/or vertical furnace operable to perform diffusions and/or oxidations on the substrate 602. The oxidation system 634 may include its own temperature control or such control may be implemented by a separate temperature system 636 effective to regulate temperature parameters within the chamber 606.

A pressure system 638 is similarly provided to selectively regulate the pressure within the chamber. The pressure system 638 may include, for example, one or more vent conduits 640 having valves 624 that can be opened and/or closed to varying degrees to assist with regulating the pressure within the chamber 606.

A CMP system 644 is included to facilitate chemical and/or mechanical polishing of the substrate 602. Slurries having varying degrees of abrasiveness can be selectively applied to the wafer via a slurry dispenser 646. One or more polishing pads (not shown) can be selectively brought into contact with the surface of the wafer and rotated relative thereto to, in conjunction with the slurry, polish back the surface of the wafer and structures forming thereon to mitigate non-uniformity, for example. An etching system 648 is similarly included to facilitate etching by providing various quantities and concentrations of etchants onto the wafer 602 via an etchant dispenser 650.

A load system 652 is also depicted as operatively connected to the chamber 606 for loading and unloading substrates (e.g., wafers) into and out of the processing chamber. The load system 652 typically is automated to load and unload the wafers into the chamber at a controlled rate. A display 654 is also included and is operatively coupled to the control system 620 for displaying, for example, a representation (e.g., graphical and/or textual) of one or more measured conditions, such as dimensions of structures forming on the wafer as well as operating parameters of one or more fabrication components acting on the wafer. A power supply 656 is also included to provide operating power to the components of the system 600. Any suitable power supply (e.g., battery, line power) may be implemented with the present invention.

In the example illustrated, one or more other sensors 658 are also included to monitor and/or measure selected processing conditions within the chamber 606. The other sensors 658 may include, for example, a temperature sensor, mass flow sensor, a pressure sensor, etc. The various other sensors 658 may provide respective signals to the control system 620 regarding the measured parameters. The control system 620 may in turn analyze the conditions indicated by the received signals to discern whether the fabrication process is progressing as desired. The control system 620 regulates the fabrication process in response to signals received from the measurement system 610 and the other sensors 658 by adapting one or more of the fabrication components (e.g., projection system 622, positioning system 626, gas distribution system 628, oxidation system 634, temperature system 636, pressure system 638, CMP system 644, etching system 648) and/or operating parameters associated therewith. The control system can thus selectively adjust one or more operating parameters of one or more of the fabrication components to mitigate undesired results, such as non-uniformity of repeating in circuit structures.

A data store 660 is also included in the example shown in FIG. 6. The data store 660 can serve, for example, as a signal (signature) library that can be populated with an abundance of signatures against which one or more measurements can be compared. Entries in the data store can be stored with respective operating parameters under which they were obtained (e.g., illumination intensity, temperature, pressure, gas distribution volume/rate) and relations can be formed to facilitate correlating process parameters. One or more measured values can be compared to one or more entries within the data store (e.g., by direct matching, interpolation or otherwise) to generate feed forward/backward control data to control one or more operating parameters of one or more the fabrication processing components to achieve a desired result. For example, the rate, concentration and/or mixture of gases distributed into the processing chamber may be selectively adjusted to achieve a desired level of film growth. This determination can also take into account the present value of one or more operating conditions such as temperature, pressure, etc. Substantially unique signatures can be obtained manually to populate the data store 660 by observing structures formed during a training session, for example. Alternatively, or in addition to manually observing values, simulation, modeling and/or artificial intelligence techniques can be employed to populate the data store with signatures against which measured values can be compared.

It is to be appreciated that the data store 660 can store data in data structures including, but not limited to one or more lists, arrays, tables, databases, stacks, heaps, linked lists and data cubes. Furthermore, the data store 660 can reside on one physical device and/or may be distributed between two or more physical devices (e.g., disk drives, tape drives, memory units). In the example shown in FIG. 6, the data store 660 is operatively coupled to the control system 620 for correlating entries therein (e.g., with other process parameters). The control system 620 may be employed to populate the data store 660 (e.g., via the measurement system 610, other sensors 658). Alternatively, the data store may be directly connected to the measurement system 610 and sensors 658 so as to by-pass the control system 620 during population.

By way of example, the control system 620 includes a processor 662, such as a microprocessor or CPU, coupled to a memory 664. The processor 662 receives data and information from the measurement system 610 and corresponding other data from the other sensors 658. The processor 662 may be operatively coupled to one or more of the fabrication components (e.g., projection system 622, positioning system 626, gas distribution system 628, oxidation system 634, temperature system 636, pressure system 638, CMP system 644, etching system 648) to facilitate selective control thereof. The processor, or CPU 662, may be any of a plurality of processors, and the manner in which the processor 662 can be programmed to carry out the functions described herein will be readily apparent to those having ordinary skill in the art based on the description provided herein.

The memory 664 is operable to store, among other things, program code executed by the processor 662 for carrying out one or more of the functions described herein. The memory may include, for example, read only memory (ROM) and random access memory (RAM). The ROM contains among other code the Basic Input-Output System (BIOS) which controls basic hardware operations of the system 600. The RAM is the main memory into which the operating system and application programs are loaded. The memory 664 may also serve as a storage medium for temporarily storing information and data including algorithms that may be useful in carrying out one or more aspects of the present invention. For mass data storage, the memory 664 may also include a hard disk drive (e.g., 50 Gigabyte hard drive), and as such may comprise some or all of the data maintained within the data store 660.

As a result, the system 600 provides for monitoring and controlling semiconductor fabrication processing, such as, for example, by monitoring the uniformity of repeating in circuit structures and well as other sensed conditions, associated with the process. The monitored conditions provide data based upon which the control system 620 may implement feedback/feed forward process control, alone or in combination with other stored data, so as to selectively adapt one or more fabrication components and/or operating parameters associated therewith to achieve a desired result, such as repeating in circuit structure uniformity, critical dimensions within acceptable tolerances and minimizing of overlay.

Turning now to FIGS. 7–9, in accordance with one or more aspects of the present invention, a wafer 702 (or one or more die located thereon) situated on a stage 704 may be logically partitioned into grid blocks to facilitate measurement of repeating in circuit structures as the wafer matriculates through a semiconductor fabrication process. This may facilitate selectively determining to what extent, if any, fabrication adjustments are necessary. Obtaining such information may also assist in determining problem areas associated with fabrication processes.

FIG. 7 illustrates a perspective view of a steppable stage 704 supporting a wafer 702. The wafer 702 may be divided into a grid pattern as shown in FIG. 8. Each grid block (XY) of the grid pattern corresponds to a particular portion of the wafer 702 (e.g., a die or a portion of a die). The grid blocks are individually monitored for fabrication progress by measuring repeating in circuit structures with scatterometry based techniques.

In FIG. 8, repeating in circuit structures on one or more respective portions of a wafer 702 ($X_1Y_1 \ldots X_{12}, Y_{12}$) are monitored with scatterometry based techniques. Exemplary measurements produced during fabrication for each grid block are illustrated as respective plots. The plots can, for example, be composite valuations of signatures of critical dimensions and/or overlay of the measured structures, as well as indications of uniformity among the forming structures. As can be seen, the measurement at coordinate $X_7Y_6$ yields a plot that is substantially higher than the respective measurements of the other portions XY. This can be indicative of non-uniformity, overlay and/or one or more critical dimension outside of acceptable tolerances. As such, fabrication components and/or operating parameters associated therewith can be adjusted accordingly to mitigate this aberrational measurement as well as repetition of this occurrence on subsequently processed wafers/die. It is to be appreciated that the wafer 702 and or one or more die located thereon may be mapped into any suitable number and/or arrangement of grid blocks to effect desired monitoring and control.

FIG. 9 is a representative table of repeating in circuit structures taken at various portions of the wafer 702 mapped to respective grid blocks. The measurements in the table can, for example, be amalgams of structure uniformity, critical dimension and overlay signatures. As can be seen, all the grid blocks, except grid block $X_7Y_6$, have measurement values corresponding to an acceptable value ($V_A$), while grid block $X_7Y_6$ has an undesired value ($V_U$). Thus, it has been determined that an undesirable fabrication condition exists at the portion of the wafer 702 mapped by grid block $X_7Y_6$. Accordingly, fabrication process components and parameters may be adjusted as described herein to adapt the fabrication process accordingly to mitigate the reoccurrence or persistence of this unacceptable condition. Alternatively, a sufficient number of grid blocks may have desirable measurements so that the single offensive grid block does not warrant scrapping the entire wafer. It is to be appreciated that fabrication process parameters may be adapted so as to maintain, increase, decrease and/or qualitatively change the fabrication of the respective portions of the wafer 702 as desired. For example, when the fabrication process has reached a pre-determined threshold level (e.g., X% of grid blocks have acceptable repeating in circuit structural uniformity, CDs and no overlay), a fabrication step may be terminated.

Figure 10:
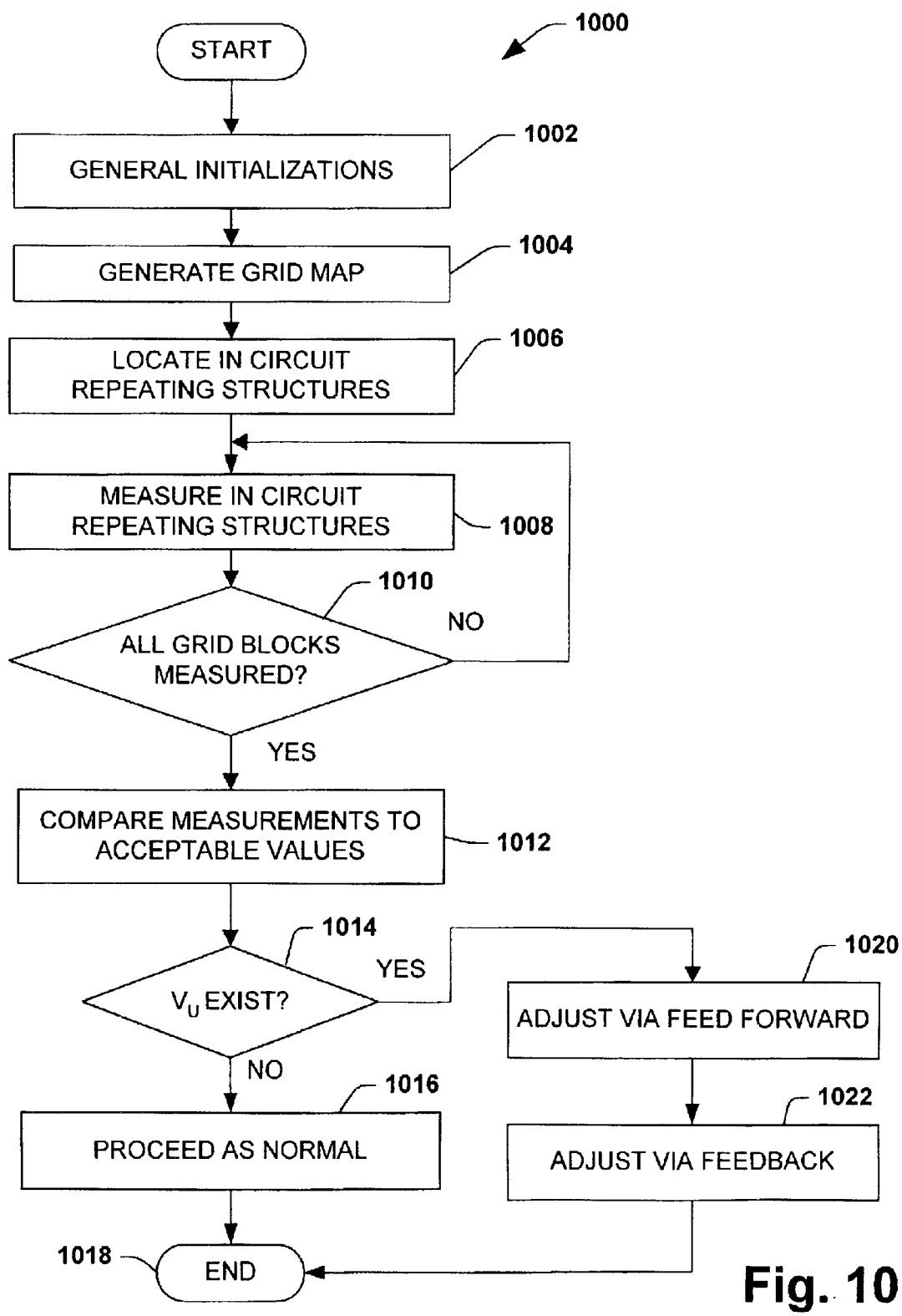
FIG. 10 is flow diagram illustrating a methodology for monitoring and controlling an IC fabrication process according to one or more aspects of the present invention.

In view of the exemplary systems shown and described above, a methodology, which may be implemented in accordance with one or more aspects of the present invention, will be better appreciated with reference to the flow diagram of FIG. 10. While, for purposes of simplicity of explanation, the methodology is shown and described as a series of function blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with one or more aspects of the present invention. It is to be appreciated that the various blocks may be implemented via software, hardware a combination thereof or any other suitable means (e.g., device, system, process, component) for carrying out the functionality associated with the blocks. It is also to be appreciated that the blocks are merely to illustrate certain aspects of the present invention in a simplified form and that these aspects may be illustrated via a lesser and/or greater number of blocks.

FIG. 10 is flow diagram illustrating a methodology 1000 for monitoring and controlling an IC fabrication process according to one or more aspects of the present invention. The methodology begins at 1002 wherein general initializations are performed. Such initializations can include, but are not limited to, establishing pointers, allocating memory, setting variables, establishing communication channels and/or instantiating one or more objects. At 1004, a grid map comprising one or more grid blocks "XY" is generated. Such grid blocks may correspond to die on the wafer and or to portions of one or more die on a wafer, for example. At 1006, repeating structures within circuits forming on the wafer are located at respective grid mapped locations. At 1008, as the wafer matriculates through the fabrication process, repeating in circuit structures are measured with scatterometry based techniques at the grid mapped locations. For example, structure heights, widths, slopes, etc. can be measured. At 1010, a determination is made as to whether measurements have been taken at all (or a sufficient number) of grid mapped locations. If the determination at 1010 is NO, then processing returns to 1008 so that additional measurements can be made. If the determination at 1010 is YES, then at 1012 the measurements are compared to acceptable values to determine if the fabrication process is progressing as planned. By way of example, the measurements can be compared to acceptable values to determine if the repeating structures are being formed uniformly, if critical dimensions are being maintained within acceptable tolerances, and/or whether overlay is occurring at the grid mapped locations. Additionally, or in the alternative, the measurements can be analyzed to produce respective signatures to serve as the basis for such determinations. These signatures can be compared to acceptable signature values for respective grid mapped locations. At 1014, a determination is made as to whether an undesired value ($V_U$) has been encountered at any one or more of the grid mapped locations (e.g., indicating that repeating in circuit structures are not being formed uniformly, that overlay is occurring and/or that one or more critical dimensions are outside of acceptable tolerances). If the determination at 1014 is NO, then at 1016 processing continues as normal. The methodology can thereafter advance to 1018 and end. If, however, the determination at 1014 is YES, meaning that an undesired value was encountered, then at 1020, one or more fabrications components and/or operating parameters associated therewith can be selectively adjusted as described herein according to feed forward control data derived from the measurements to mitigate or remedy the situation. For example, an exposing source can be turned off and/or data generated by sophisticated modeling techniques can be fed forward to post exposure baking and/or development stages to control processing parameters such as bake time and/or temperature. At 1022, control data derived from the measurements can also be feed back to adjust one or more fabrications components and/or operating parameters associated therewith to mitigate re-occurrence of the undesired event during subsequent processing. For instance, stepped alignment of the wafer can be adjusted to facilitate proper placement of structures on subsequently processed dies. Similarly, exposure time and/or intensity can be controlled so that structures having a proper slope is formed within a photoresist layer. The methodology then ends at 1018. As mentioned above, events can occur in orders different from that depicted in FIG. 10. For example, measurements taken, as at 1006, can be compared to acceptable values, as at 1012, prior to determining whether measurements have been taken at all grid mapped locations, as at 1010.

Figure 11:
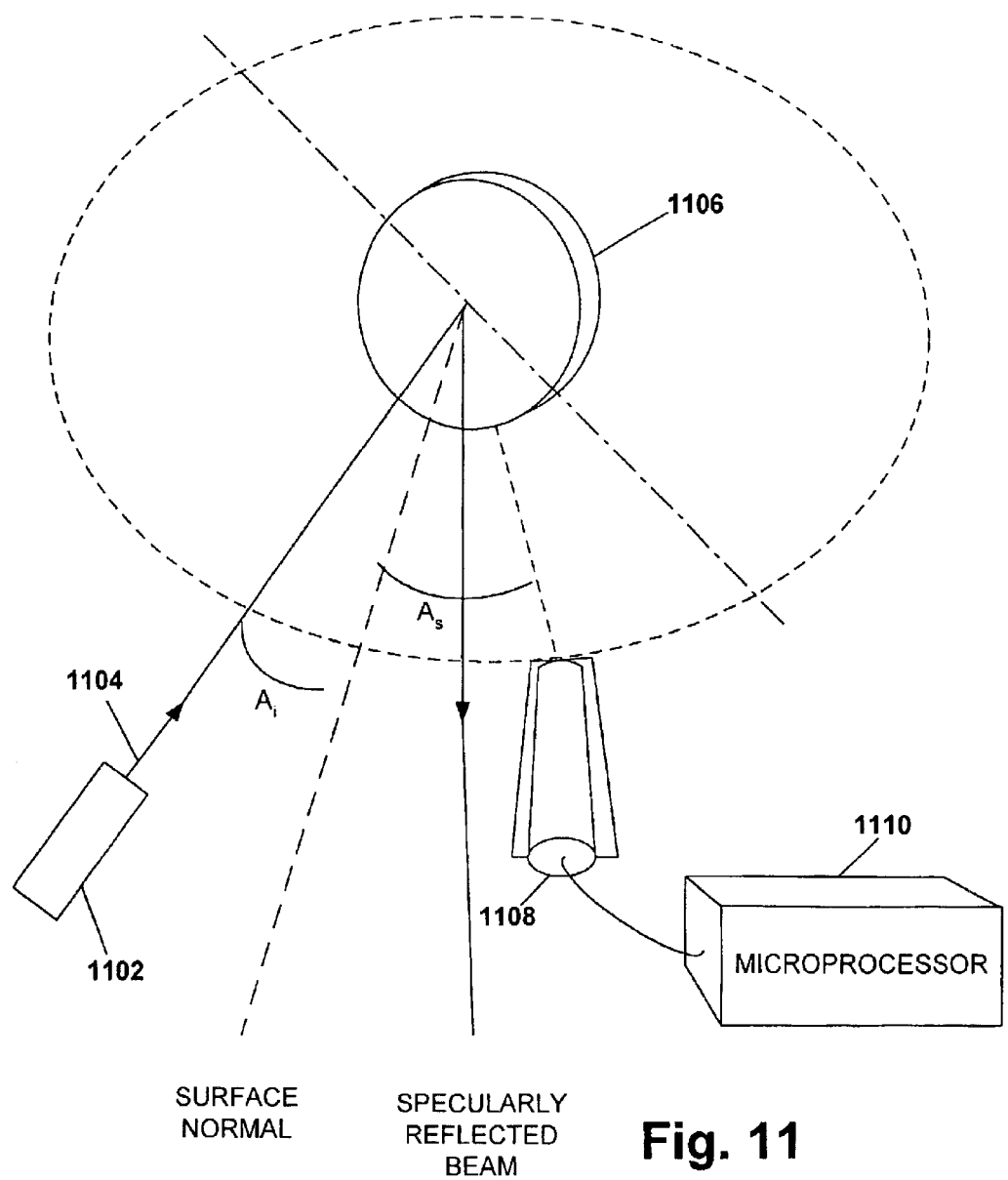
FIG. 11 illustrates an exemplary scatterometry system suitable for implementation with one or more aspects of the present invention.

FIG. 11 illustrates an exemplary scatterometry system suitable for implementation with one or more aspects of the present invention. Light from a laser 1102 is brought to focus in any suitable manner to form a beam 1104. A sample, such as a wafer 1106, is placed in the path of the beam 1104 and a photo detector or photo multiplier 1108 of any suitable construction. Different detector methods and arrangements may be employed to determine the scattered and/or reflected power. A microprocessor 1110, of any suitable design, may be used to process detector readouts, including, but not limited to, intensity properties of the specularly reflected light, polarization properties of the specularly reflected light, and angular locations of different diffracted orders. Thus, light reflected from the sample 1106 may be accurately measured.

Concepts of scatterometry and how they are employed in accordance with one or more aspects of the present invention are discussed with respect to FIGS. 12–17. Scatterometry is a technique for extracting information about a surface upon which an incident light has been directed. Scatterometry is a metrology that relates the geometry of a sample to its scattering effects. Scatterometry is based optical diffraction responses. Scatterometry can be employed to acquire information concerning properties including, but not limited to, horizontal/vertical alignment/shifting/compression/stretching, dishing, erosion, profile and critical dimensions of a surface and/or features present on a surface. The information can be extracted by comparing the phase and/or intensity of a reference light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the planarity of the surface, features on the surface, voids in the surface, the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature or stored value) library of intensity/phase signatures, a determination can be made concerning the properties of the surface. Such substantially unique intensity/phase signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N = n - jk, \text{ where } j \text{ is an imaginary number.}$$

The signal (signature) library can be constructed from observed intensity/phase signatures and/or signatures generated by modeling and simulation. By way of illustration, when exposed to a first incident light of known intensity, wavelength and phase, a wafer can generate a first intensity/phase signature. Observed signatures can be combined with simulated and modeled signatures to form a signal (signature) library. Simulation and modeling can be employed to produce signatures against which measured intensity/phase signatures can be matched. In one exemplary aspect of the present invention, simulation, modeling and observed signatures are stored in a signal (signature) data store. Thus, when intensity/phase signals are received from scatterometry detecting components, the intensity/phase signals can be pattern matched, for example, to the library of signals to determine whether the signals correspond to a stored signature.

Figure 12:
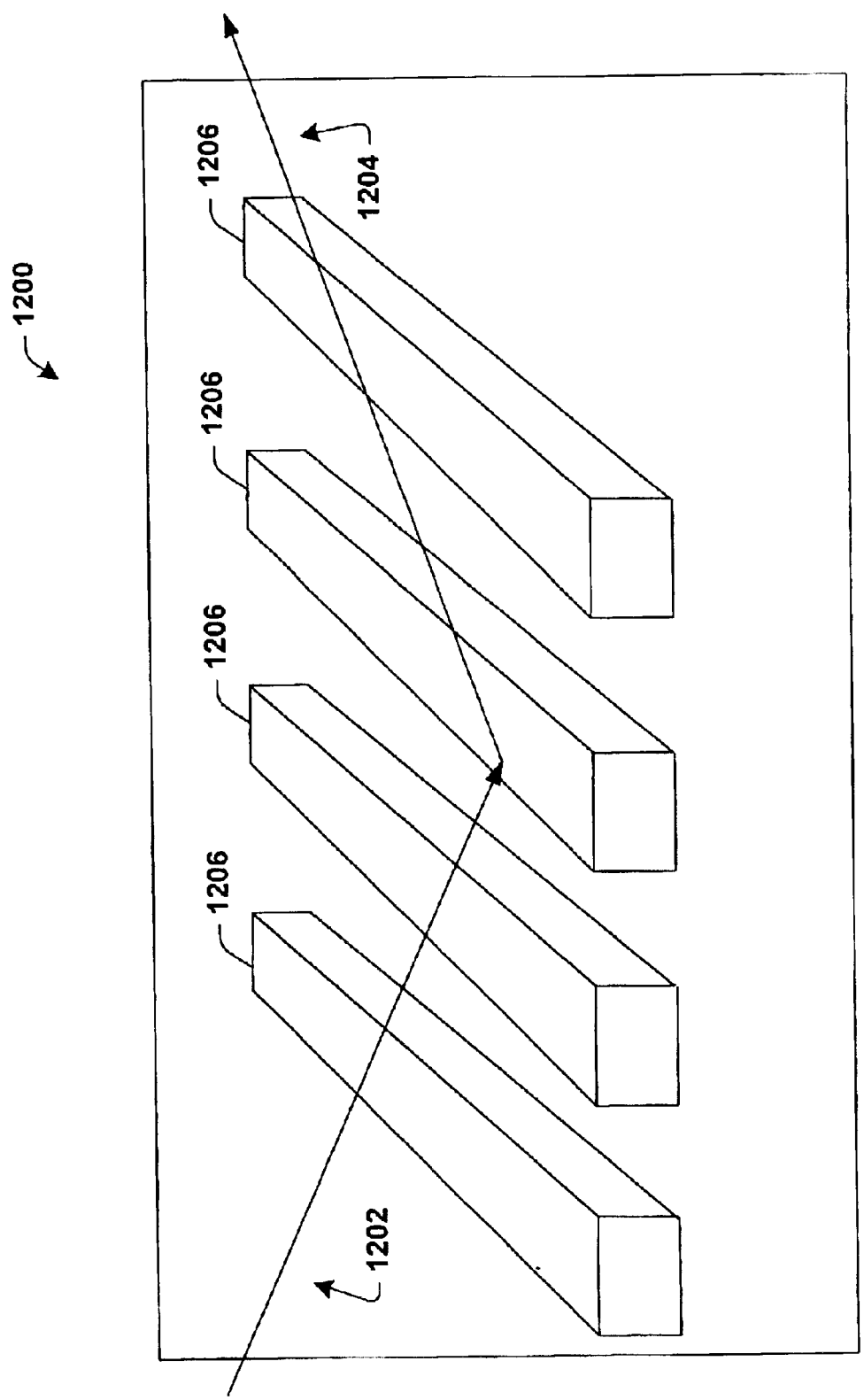
FIG. 12 is a simplified perspective view of an incident light reflecting off a surface in accordance with one or more aspects of the present invention.

To illustrate the principles described above, reference is now made to FIGS. 12 through 17. Referring initially to FIG. 12, an incident light 1202 is directed at a surface 1200, upon which one or more features 1206 may exist. The incident light 1202 is reflected as reflected light 1204. The properties of the surface 1200, including but not limited to, thickness, uniformity, planarity, chemical composition and the presence of features, can affect the reflected light 1204. The features 1206 are raised upon the surface 1200, but could also be recessed therein. The phase and/or intensity of the reflected light 1204 can be measured and plotted, as partially shown, for example, in FIG. 17. Such plots can be employed to compare measured signals with signatures stored in a signature library using techniques like pattern matching, for example.

Figure 13:
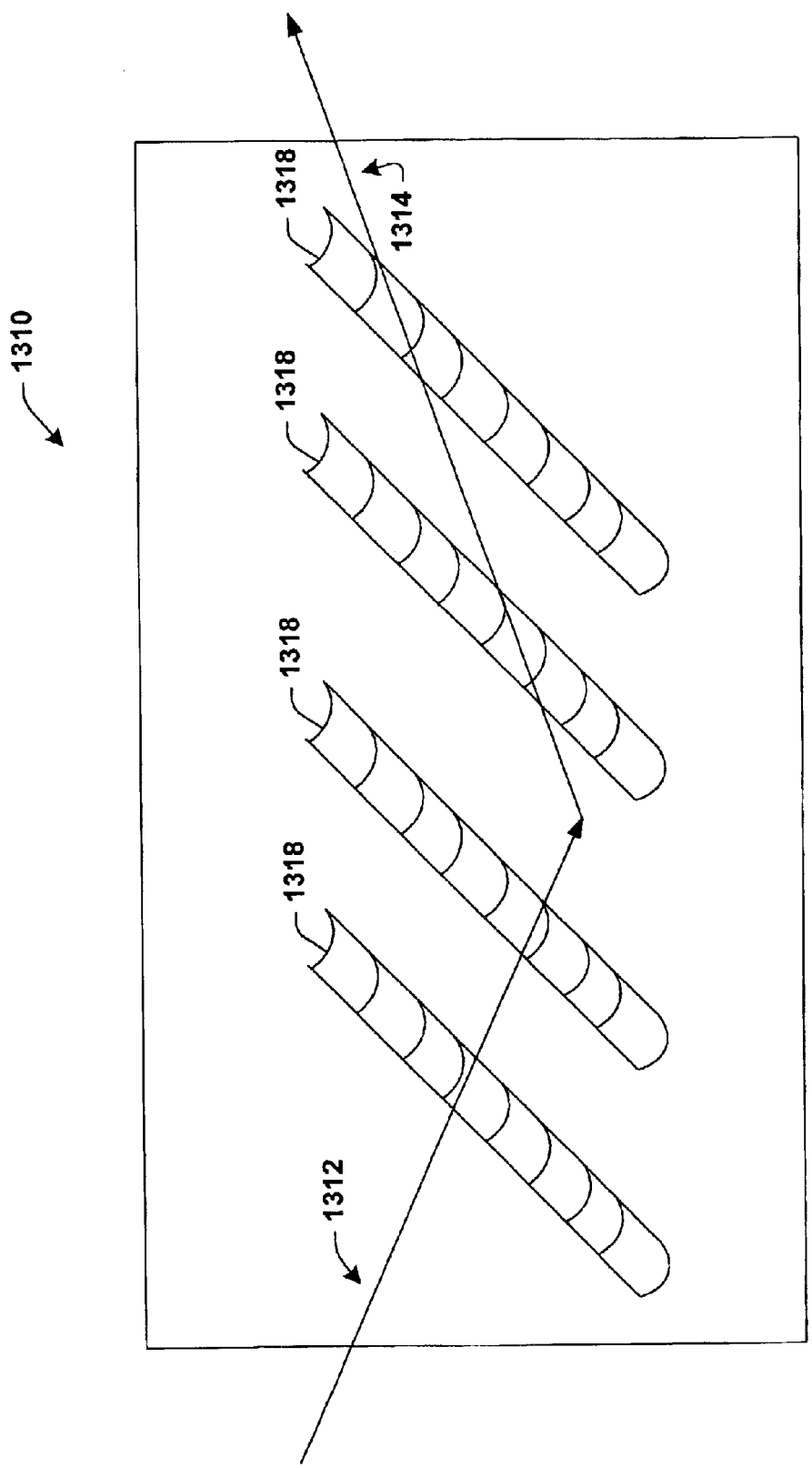
FIG. 13 is another simplified perspective view of an incident light reflecting off a surface in accordance with one or more aspects of the present invention.

Referring now to FIG. 13, an incident light 1312 is directed onto a surface 1310 upon which one or more depressions 1318 appear. The incident light 1312 is reflected as reflected light 1314. Depressions 1318 will affect the scatterometry signature to produce a substantially unique signature. It is to be appreciated that scatterometry can be employed to measure, among other things, features appearing on a surface, features appearing in a surface, features emerging in a pattern.

Figure 14:
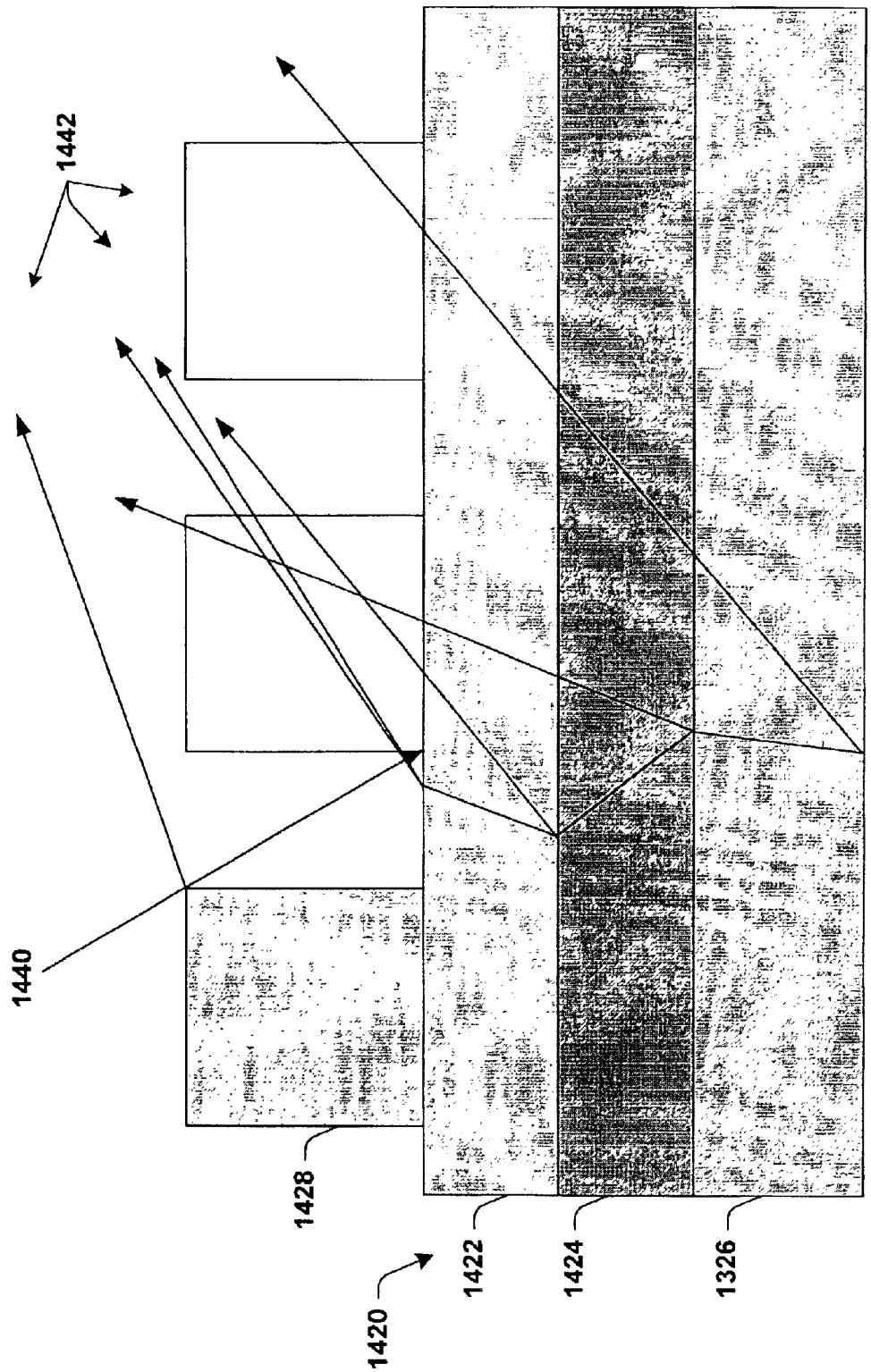
FIG. 14 illustrates a complex reflected and refracted light produced when an incident light is directed onto a surface in accordance with one or more aspects of the present invention.

Turning now to FIG. 14, complex reflections and refractions of an incident light 1440 are illustrated. The reflection and refraction of the incident light 1440 can be affected by factors including, but not limited to, the presence of one or more features 1428 and the composition of the substrate 1420 upon which the features 1428 reside. For example, properties of the substrate 1420 including, but not limited to the thickness of a layer 1422, the chemical properties of the layer 1422, the opacity and/or reflectivity of the layer 1422, the thickness of a layer 1424, the chemical properties of the layer 1424, the opacity and/or reflectivity of the layer 1424, the thickness of a layer 1426, the chemical properties of the layer 1426, and the opacity and/or reflectivity of the layer 1426 can affect the reflection and/or refraction of the incident light 1440. Thus, a complex reflected and/or refracted light 1442 may result from the incident light 1440 interacting with the features 1428, and/or the layers 1422, 1424 and 1426. Although three layers 1422, 1424 and 1426 are illustrated in FIG. 14, it is to be appreciated that a substrate can be formed of a greater or lesser number of such layers.

Figure 15:
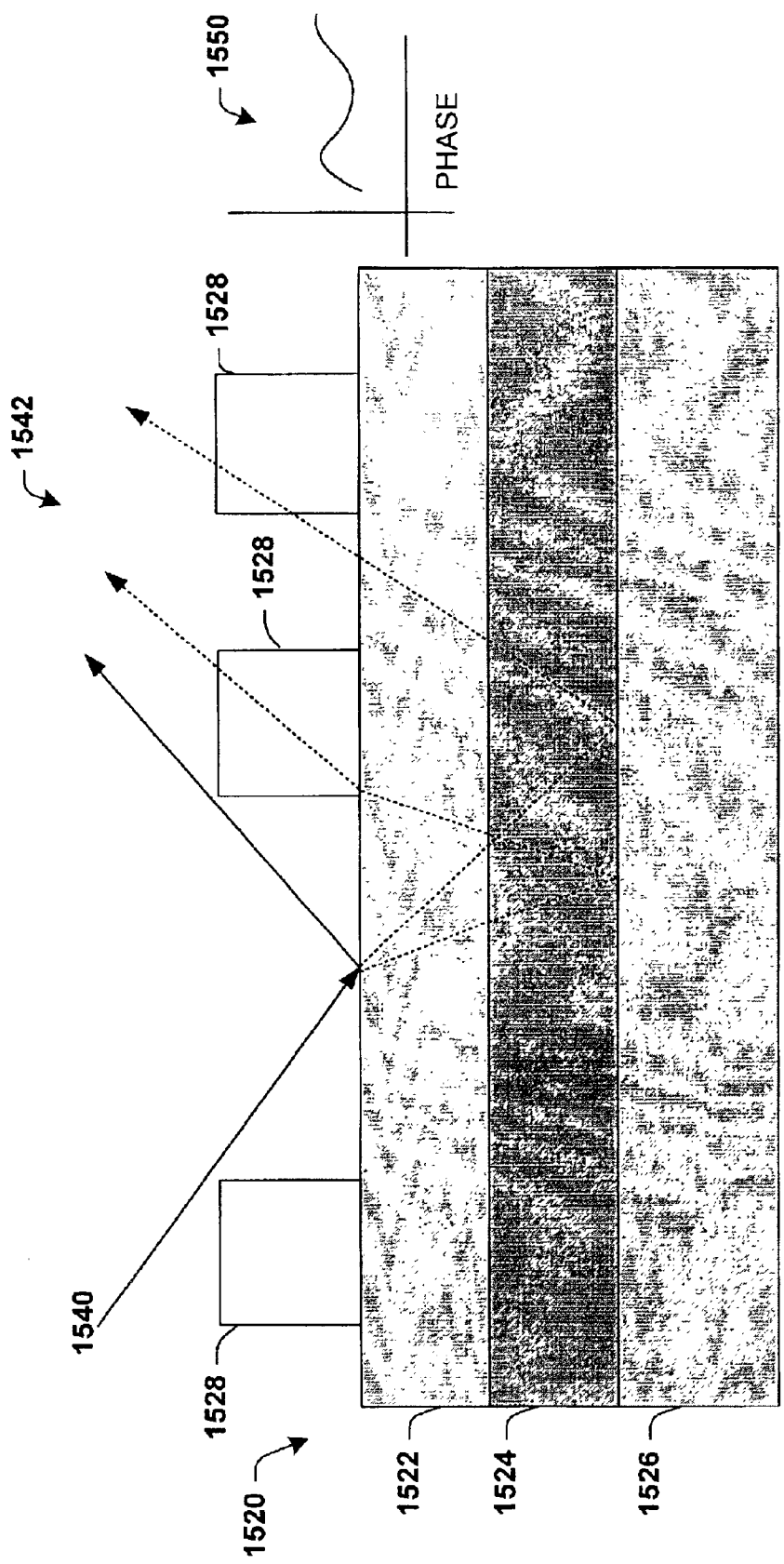
FIG. 15 illustrates another complex reflected and refracted light produced when an incident light is directed onto a surface in accordance with one or more aspects of the present invention.
Figure 16:
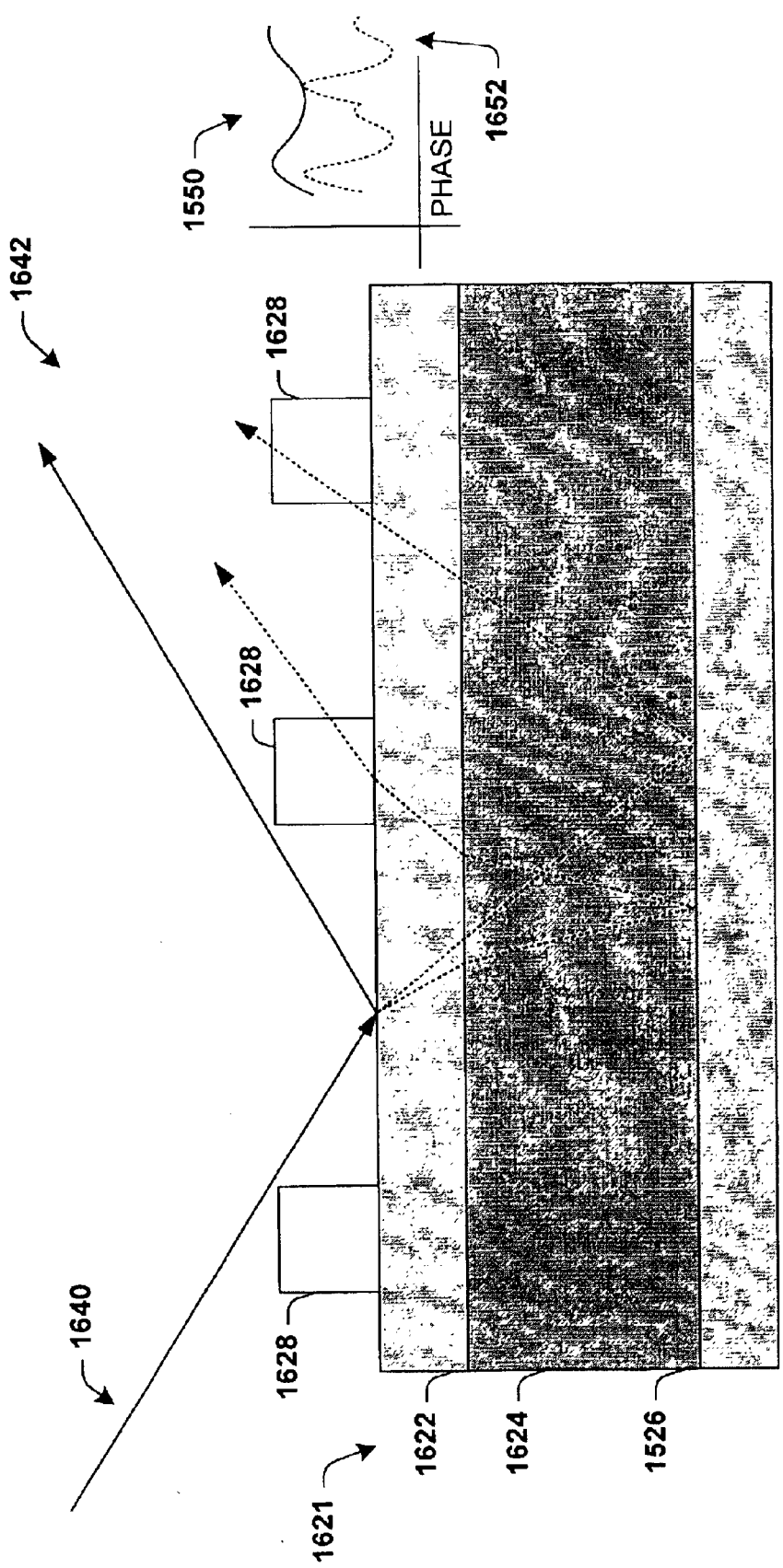
FIG. 16 illustrates yet another complex reflected and refracted light produced when an incident light is directed onto a surface in accordance with one or more aspects of the present invention.
Figure 17:
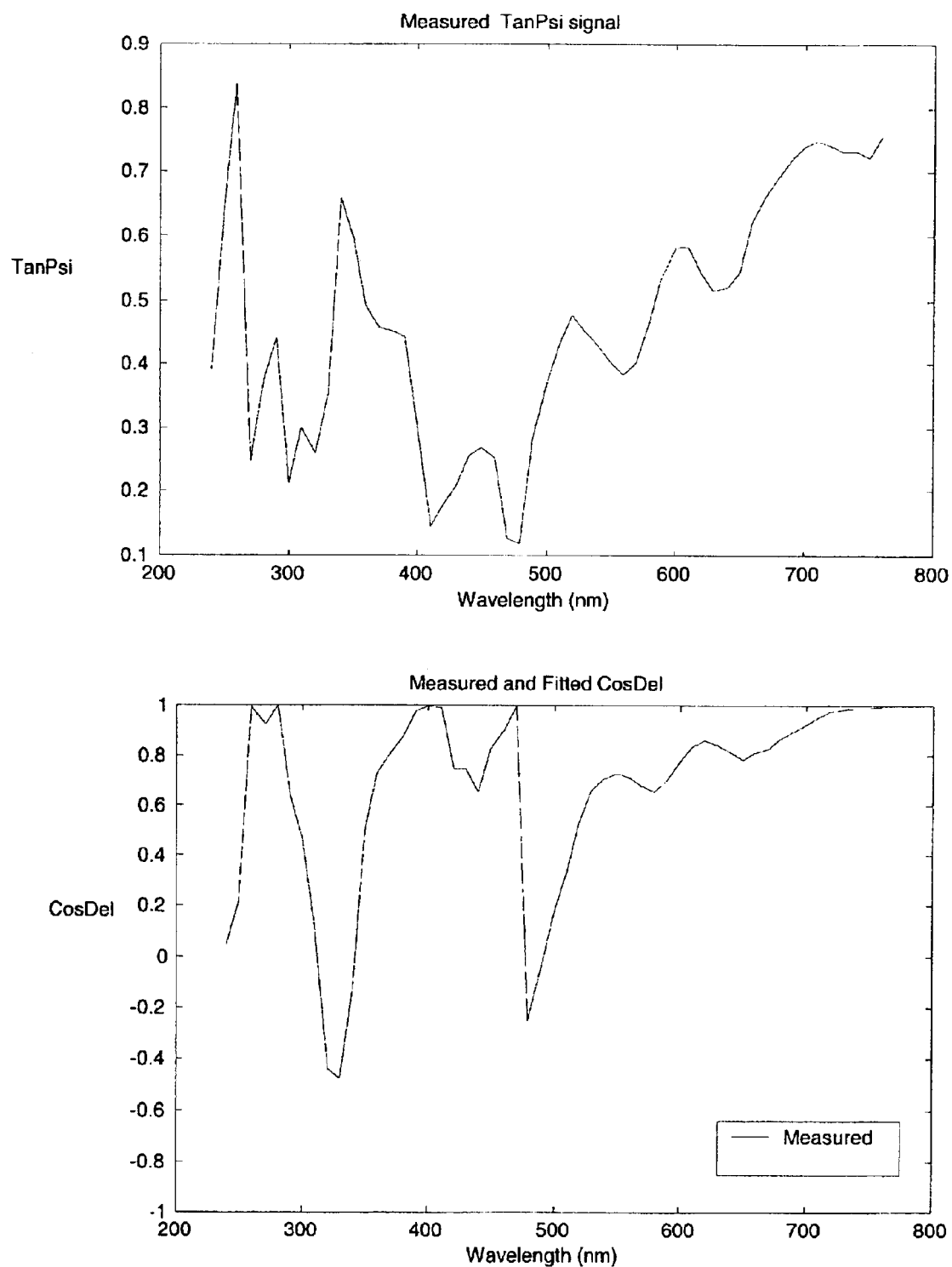
FIG. 17 illustrates phase and/or intensity signals recorded from a complex reflected and refracted light produced when an incident light is directed onto a surface in accordance with one or more aspects of the present invention.

Turning now to FIG. 15, one of the properties from FIG. 14 is illustrated in greater detail. The substrate 1520 can be formed of one or more layers 1522, 1524 and 1526. The phase 1550 of the reflected and/or refracted light 1542 from incident light 1540 can depend, at least in part, on the thickness of a layer, for example, the layer 1524. Thus, in FIG. 16, the phase 1652 of the reflected light 1642 differs from the phase 1550 due, at least in part, to the different thickness of the layer 1624 in FIG. 16.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

Using scatterometry in implementing one or more aspects of the present invention facilitates a relatively non-invasive approach to obtaining desired measurements, which can, in turn, be utilized to facilitate achieving desired results in presently occurring or subsequent processing cycles.

Described above are preferred aspects of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system that monitors and controls a semiconductor fabrication process comprising:
 a measurement system that interacts via scatterometry based techniques with repeating in circuit structures that are formed on at least a portion of a wafer as the wafer matriculates through the fabrication process; and
 a control system operatively coupled to the measurement system and one or more fabrication components that selects at least one fabrication component operable to compensate for an unacceptable measured value of one or more in circuit structures and selectively adjusts one or more of the at least one fabrication component and operating parameters associated with the at least one fabrication component to adapt the fabrication process in response to readings taken by the measurement system.

2. The system of claim 1 wherein the repeating in circuit structures comprise substantially elongated marks.

3. The system of claim 2 wherein the structures are oriented substantially in parallel to one another.

4. The system of claim 3 wherein the structures correspond to one or more portions of a memory core area of an integrated circuit (IC).

5. The system of claim 1 wherein the structures correspond to one or more portions of an SRAM memory cell.

6. The system of claim 5 wherein the readings taken by the measurement system are compared to at least one of predetermined data and historical test data.

7. The system of claim 1 wherein the measurement system periodically measures at least one of critical dimensions and overlay.

8. The system of claim 7 wherein the measurement system periodically measures at least one of height, width and slope of the repeating in circuit structures to facilitate a determination of whether the structures are being formed uniformly within the wafer.

9. The system of claim 1 wherein the measurement system includes one or more light emitters that direct light incident to the repeating in circuit structures; and
 one or more light detecting components that collect light reflected from the repeating in circuit structures, the reflected light varying in at least one of angle, intensity, phase and polarization as the fabrication process progresses and the repeating in circuit structures evolve.

10. The system of claim 9 wherein output from one or more of the light detecting components can be analyzed to generate one or more signatures for comparison to one or more stored signatures to determine at least one of whether one or more of the repeating in circuit structures are being formed uniformly, whether one or more critical dimensions fall outside of acceptable tolerances and whether overlay error is occurring.

11. The system of claim 1 wherein the control system can control at least one of alignment, exposure, post exposure baking, development, photolithography, etching, polishing, deposition, exposure time, exposure intensity, exposure magnification, exposure de-magnification, movement via a stepper motor, temperatures associated with the process, pressures associated with the process, concentration of gases applied to the process, concentration of chemicals applied to the process, flow rates of gases applied to the process, flow rates of chemicals applied to the process, excitation voltages associated with the process, illumination time, illumination intensity, concentration of slurry applied during CMP, rate of flow of slurry applied during CMP, degree of abrasiveness of slurry applied dining CMP, pressure applied during CMP, baking time, baking temperatures and etchant concentrations.

12. A method for monitoring and controlling a semiconductor fabrication process comprising:
  measuring via scatterometry based techniques one or more repeating in circuit structures forming on at least a portion of a wafer as the wafer undergoes the fabrication process;
  developing control data based upon the measurements;
  feeding the control data at least one of forward and backward to one or more fabrication components; and
  selectively adjusting one or more operating parameters associated with the one or more fabrication components to adapt the fabrication process to compensate for an unacceptable measured value according to the control data.

13. The method of claim 12 wherein the fabrication components include at least one of a projection system, positioning system, gas distribution system, oxidation system, temperature system, pressure system, CMP system and etching system.

14. The method of claim 12 further comprising;
  locating one or more repeating in circuit structures for measurement.

15. The method of claim 12 further comprising;
  measuring at least one of height, width and slope of the repeating in circuit structures.

16. The method of claim 15 further comprising;
  determining at least one of whether one or more of the repeating in circuit structures are being formed uniformly, whether one or more critical dimensions fall outside of acceptable tolerances and whether overlay error is occurring.

17. The method of claim 12 wherein the repeating in circuit structures comprise substantially elongated marks oriented substantially in parallel to one another and correspond to one or more portions of a memory core area of an integrated circuit (IC).

18. The method of claim 12 further comprising:
  determining whether to discard the wafer or portions thereof based on a cost benefit analysis.

19. The method of claim 12 wherein the structures correspond to one or more portions of an SRAM memory cell.

20. The method of claim 12 further comprising:
  mapping the wafer into one or more grids; and
  measuring the repeating in circuit structures at the grid mapped locations.

21. The method of claim 12 further comprising:
  directing light incident to the structures;
  collecting light reflected from the structures; and
  detecting variations in at least one of angle, intensity, phase and polarization of the reflected light as the fabrication process progresses and the repeating in circuit structures evolve.

22. The method of claim 21 further comprising.
  developing signatures from the collected light;
  comparing the signatures to one or more stored signatures to determine at least one of whether one or more of the repeating in circuit structures are being formed uniformly, whether one or more critical dimensions fall outside of acceptable tolerances and whether overlay is occurring.

23. A system that monitors and controls a semiconductor fabrication process comprising:
  means for directing light incident to repeating in circuit structures forming within at least a portion of a wafer undergoing the fabrication process;
  means for collecting light reflected from the structures;
  means for adjusting one or more fabrication components or one or more operating parameters associated with the fabrication components to adapt the fabrication process in response to the collected light; and
  means for selectively discarding the wafer or a portion thereof based on cost benefit analysis.

24. The system of claim 23 further comprising:
  means for analyzing the reflected light to generate one or more signatures; and
  means for comparing the signatures to one or more stored signatures to determine at least one of whether one or more of the repeating in circuit structures are being formed uniformly, whether one or more critical dimensions fall outside of acceptable tolerances and whether overlay is occurring.

25. The system of claim 24 further comprising:
  means for locating one or more repeating in circuit structures for measurement.

* * * * *